US011433191B2

(12) United States Patent
Fallon et al.

(10) Patent No.: US 11,433,191 B2
(45) Date of Patent: Sep. 6, 2022

(54) APPARATUS FOR HEATING AEROSOL GENERATING MATERIAL AND A CARTRIDGE FOR THE APPARATUS

(71) Applicant: BRITISH AMERICAN TOBACCO (INVESTMENTS) LIMITED, London (GB)

(72) Inventors: Gary Fallon, London (GB); Andrew Bray, London (GB); Jeonghwan Park, London (GB); Kav Ghanouni, London (GB); Richard Hepworth, London (GB); Walid Abi Aoun, London (GB); Karl Kaljura, London (GB)

(73) Assignee: Nicoventures Trading Limited, London (GB)

( * ) Notice: Subject to any disclaimer, the term of this patent is extended or adjusted under 35 U.S.C. 154(b) by 823 days.

(21) Appl. No.: 16/086,991

(22) PCT Filed: Mar. 30, 2017

(86) PCT No.: PCT/EP2017/057630
§ 371 (c)(1),
(2) Date: Sep. 20, 2018

(87) PCT Pub. No.: WO2017/167932
PCT Pub. Date: Oct. 5, 2017

(65) Prior Publication Data
US 2019/0098930 A1    Apr. 4, 2019

(30) Foreign Application Priority Data

Mar. 30, 2016 (GB) ...................................... 1605357

(51) Int. Cl.
*A24F 40/30* (2020.01)
*A24F 40/42* (2020.01)
(Continued)

(52) U.S. Cl.
CPC ......... *A61M 15/0028* (2013.01); *A24F 40/30* (2020.01); *A24F 40/42* (2020.01);
(Continued)

(58) Field of Classification Search
CPC . A61M 15/0028; A61M 15/003; A24F 40/00; A24F 40/10; A24F 40/30; A24F 40/40; A24F 40/42
See application file for complete search history.

(56) References Cited

U.S. PATENT DOCUMENTS

2009/0293888 A1    12/2009  Williams
2014/0216485 A1*    8/2014  Egoyants ................ A24F 40/40
                                                    131/329
(Continued)

FOREIGN PATENT DOCUMENTS

CA    2933596 A1    8/2015
CA    2937974        8/2015
(Continued)

OTHER PUBLICATIONS

International Search Report and Written Opinion, Application No. PCT/EP2017/057630, dated Jul. 20, 2017, 2 pages.
(Continued)

*Primary Examiner* — Alex B Efta
(74) *Attorney, Agent, or Firm* — Patterson Thuente Pedersen P.A.

(57) ABSTRACT

There is described a cartridge for use with an apparatus for heating aerosol generating material to volatilize at least one component of the aerosol generating material. The cartridge includes a first body defining a first chamber and aerosol generating material is located within the first chamber. The first body includes a first base including a sheet of heat conductive material and has a first outer surface and at least a major portion of the first outer surface is for contacting a (Continued)

first heating surface of a heater of the apparatus for heating the aerosol generating material within the first chamber.

25 Claims, 18 Drawing Sheets

(51) Int. Cl.
    *A24F 40/46*     (2020.01)
    *A61M 15/06*     (2006.01)
    *A61M 15/00*     (2006.01)
    *A61M 11/04*     (2006.01)
    *A24F 40/10*     (2020.01)

(52) U.S. Cl.
    CPC ........... *A24F 40/46* (2020.01); *A61M 11/042* (2014.02); *A61M 15/06* (2013.01); *A24F 40/10* (2020.01); *A61M 15/0036* (2014.02); *A61M 2205/3334* (2013.01); *A61M 2205/8206* (2013.01)

(56) References Cited

U.S. PATENT DOCUMENTS

2017/0136196 A1*   5/2017   Davidson ................ A61P 21/00
2017/0150755 A1*   6/2017   Batista .................... A24F 40/42

FOREIGN PATENT DOCUMENTS

| | | |
|---|---|---|
| CA | 2951105 A1 | 1/2016 |
| CN | 104768407 A | 7/2015 |
| EA | 019736 B1 | 5/2014 |
| JP | 2014525237 A | 9/2014 |
| JP | 2015532828 A | 11/2015 |
| RU | 2012137713 A | 3/2014 |
| WO | WO-2011095781 A1 | 8/2011 |
| WO | WO-2015100361 A1 | 7/2015 |
| WO | WO 2015/116934 | 8/2015 |
| WO | WO-2015117700 A1 | 8/2015 |
| WO | WO-2015175568 A1 | 11/2015 |
| WO | WO-2016005533 A1 | 1/2016 |

OTHER PUBLICATIONS

International Preliminary Report on Patentability for Application No. PCT/EP2017/057630, dated Oct. 11, 2018, 9 pages.

Notice of Reasons for Rejection for Japanese Application No. 2018-548172, dated Nov. 26, 2019, 11 pages.

Office Action dated Jul. 3, 2020 for Chinese Application No. 201780018612.5, 23 pages.

* cited by examiner

APPARATUS FOR HEATING AEROSOL GENERATING MATERIAL AND A CARTRIDGE FOR THE APPARATUS

PRIORITY CLAIM

The present application is a National Phase entry of PCT Application No. PCT/EP2017/057630, filed Mar. 30, 2017, which claims priority from GB Patent Application No. 1605357.1, filed Mar. 30, 2016, each of which is hereby fully incorporated herein by reference.

TECHNICAL FIELD

The present disclosure relates to an apparatus arranged to heat aerosol generating material and a cartridge for the apparatus.

BACKGROUND

Smoking articles such as cigarettes, cigars and the like burn tobacco during use to create tobacco smoke. Attempts have been made to provide alternatives to these smoking articles by creating products that release compounds without actually combusting and hence which do not create smoke or an aerosol as a result of degradation of, for example, tobacco by combustion or the process of burning. Examples of such products are so-called heat-not-burn products, tobacco heating products or tobacco heating devices, which release compounds, which may form an aerosol, by heating, but not burning, aerosol generating material. The aerosol generating material may be for example tobacco or other non-tobacco products, which may or may not contain nicotine.

SUMMARY

In accordance with some embodiments described herein, there is provided a cartridge for use with an apparatus for heating aerosol generating material to volatilize at least one component of the aerosol generating material, the cartridge comprising: a first body defining a first chamber, wherein the first body comprises a first base comprising a sheet of heat conductive material and having a first outer surface; and aerosol generating material located within the first chamber; and wherein at least a major portion of the first outer surface of the first base is adapted to contact a first heating surface of a heater of the apparatus for heating the aerosol generating material within the first chamber and wherein the first base is substantially parallel to a longitudinal axis of the first body.

The sheet of heat conductive material may be flexible and may comprise metal foil. In other example, the sheet of heat conductive material may be non-flexible.

The first body may comprise a first cover attached to the first base, wherein the first cover and the first base define the first chamber.

The first cover may comprise a plastics or polymide material.

In use, the first body comprises an inlet for enabling air to flow into the first chamber and an outlet, spaced apart from the inlet, to enable at least one volatilized component of the aerosol generating material and/or an aerosol to flow out of the first chamber.

The cartridge may further comprise: a second body defining a second chamber, wherein the second body comprises a second base comprising a sheet of heat conductive material having a second outer surface; and aerosol generating material located within the second chamber; and wherein at least a major portion of the second outer surface of the second base is adapted to contact a second heating surface of the heater of the apparatus and wherein the second base is substantially parallel to a longitudinal axis of the second body.

The first base and the second base may be connected together to enable relative pivotal movement of the first base and the second base so that a user can bring the first outer surface into contact with the first heating surface of the heater and the second outer surface into contact with the second heating surface of the heater.

The first base and the second base may be connected along a first line of weakening to enable the relative pivotal movement.

The first base and the second base may be, in a pre-use configuration, connected at respective sides of the first base and the second base that are substantially perpendicular to a longitudinal axis of the cartridge.

The second body may comprise a second cover attached to the second base, wherein the second cover and the second base define the second chamber and wherein, the first cover and the second cover are, in the pre-use configuration, connected along a second line of weakening which ruptures when the first base and the second base undergo relative pivotable movement, whereby the first cover and the second cover are separated to provide an a volatilized material and/or aerosol outlet for the first cover and a volatilized material and/or aerosol outlet for the second cover.

The first base may comprise a first piercer for piercing the second base to provide an air inlet for the second chamber and the second base may comprise a second piercer for piercing the first base to provide an air inlet for the first chamber.

The first base and the second base may be, in a pre-use configuration, connected at respective sides of the first base and the second base that that are substantially parallel to a longitudinal axis of the cartridge.

In accordance with some embodiments described herein, there is also provided apparatus for heating aerosol generating material to volatilize at least one component of the aerosol generating material, the apparatus comprising: a housing comprising a heater, the heater comprising at least a first heating surface, the first heating surface adapted to contact at least a major portion of a heat conductive base of a first body of a cartridge that is insertable into the housing and wherein the heater extends substantially parallel to a longitudinal axis of the apparatus, whereby in use, the heater heats aerosol generating material in a chamber defined by the first body to volatilize at least one component of the aerosol generating material.

The heater may comprise a heating plate that comprises the first heating surface.

The first heating surface may be convex.

The apparatus may further comprise a mouthpiece having a mouthpiece outlet and wherein the housing comprises at least one air inlet, wherein in use, when a user draws on the outlet of the mouthpiece, air flows through the at least one air inlet of the housing and through an inlet of the first body and a mixture of air and at least one volatilized component of the aerosol generating material and/or aerosol flows out of an outlet of the first body.

The apparatus may comprise a first piercer for piercing the first body when the cartridge is inserted in the apparatus to provide one of the inlet of the first body and the outlet of the first body.

The apparatus may comprise a second piercer for piercing the first body when the cartridge is inserted in the apparatus to provide the other of the inlet of the first body and the outlet of the first body.

The apparatus may comprise a second piercer for piercing the first body when the cartridge is inserted in the apparatus to provide the other of the inlet of the first body and the outlet of the first body.

The heater may comprise a second heating surface, the second heating surface for contacting at least a major portion of the heat conductive base of a second body of the cartridge that is insertable into the housing, whereby in use, the heater heats aerosol generating material in a chamber defined by the second body to volatilize at least one component of the aerosol generating material.

The heater may be a heater plate that defines the first heating surface and a second heating surface, wherein the first and second heating surfaces are opposite surfaces of the heater plate, and wherein the second heating surface is for contacting at least a major portion of a second heat conductive base of a second body of the cartridge that is insertable into the housing, whereby in use, the heater heats aerosol generating material in a chamber defined by the first body and a chamber defined by the second body to volatilize at least one component of the aerosol generating material in the chambers.

BRIEF DESCRIPTION OF THE DRAWINGS

Embodiments of the disclosure will now be described, by way of example only, with reference to the accompanying drawings, in which.

DETAILED DESCRIPTION

Figure 1:
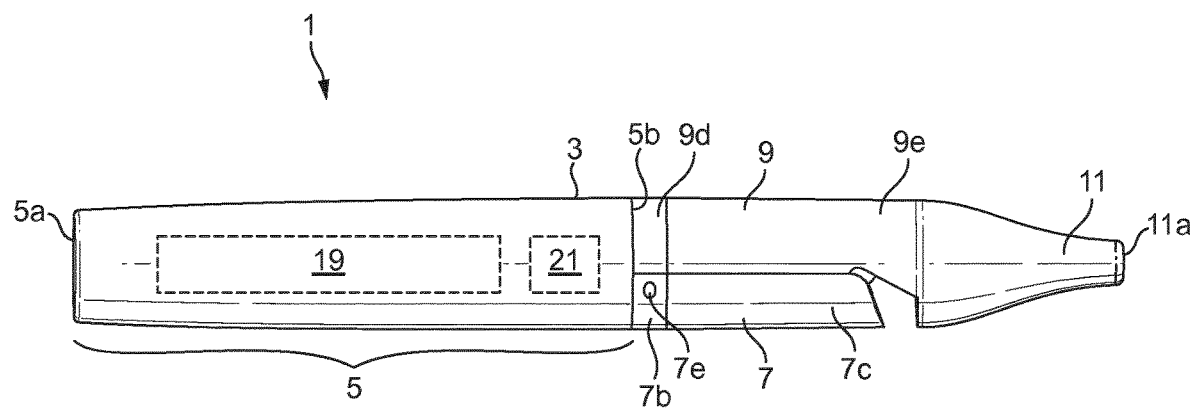
FIG. 1 shows a schematic side view of a first example of an apparatus for heating an aerosol generating material.

As used herein, the term "aerosol generating material" includes materials that provide volatilized components upon heating. "Aerosol generating material" includes any tobacco-containing material and may, for example, include one or more of tobacco, tobacco derivatives including tobacco extracts, expanded tobacco, reconstituted tobacco or tobacco substitutes. "Aerosol generating material" also may include other, non-tobacco, products, including for example flavorants, which, depending on the product, may or may not contain nicotine, filler materials such as chalk and/or sorbent materials, glycerol, propylene glycol or triacetin. The aerosol generating material may also include a binding material, for example, sodium alginate.

Referring to FIGS. 1 to 6, there is shown a first example of an apparatus 1 and a cartridge 100 that is insertable within the apparatus 1. The apparatus 1 is arranged to heat aerosol generating material (not shown) contained within the cartridge 100 when the cartridge 100 is inserted inside the apparatus 1 to volatilize at least one component of the aerosol generating material.

The apparatus 1 is a so-called "tobacco-heating-product" apparatus. The apparatus 1 in this example is generally elongate and comprises a generally tubular housing 3. The tubular housing 3 comprises a main housing section 5, a heater support section 7, a lid section 9 and a mouth piece 11 comprising an outlet 11a.

These sections of the apparatus 1 may comprise any suitable material or materials, for example, plastic or metal or combinations thereof. The mouthpiece 11 (or at least the tip of the mouthpiece 11) may comprise a material that feels comfortable to the lips, for example, suitable plastics or silicone rubber based materials.

The main housing section 5 comprises first 5a and second 5b longitudinal ends. The first end 5a defines a distal end of the whole of the apparatus 1 and the second end 5b is located at approximately just over half of the way along the length of the apparatus 1.

The heater support section 7 extends from the second 5b longitudinal end of the main housing section 5 and defines a platform 7a (most clearly seen in FIGS. 3, 4 and 5) that supports a heater 13. The heater support section 7 may, as is the case in this example, comprise a plurality 7b, 7c of interconnected sections, one of which 7b is connected to the main housing section 5, or the heater support section 7 may be a single-piece section.

The heater support section 7 and the lid section 9 are connected by a hinge arrangement 15 (best seen in FIG. 4) that is arranged to enable the lid section 9 to pivot with respect to the heater support section 7, about the hinge arrangement 15, between a closed position shown in FIG. 1 and an open position shown in FIGS. 2 to 5. The lid section 9 may, as is the case in this example, comprise a plurality 9d, 9e of interconnected sections, one of which 9e is connected to the mouthpiece 11, or the lid section 9 may be a single piece section.

The hinge arrangement 15 is arranged along an edge portion 7d of the heater support section 7 and is aligned transverse to a longitudinal axis of the apparatus 1. When the lid section 9 is in the open position, the lid section 9 defines an open channel 8 (see FIG. 3) into which a cartridge 100 can be inserted or from which it can be removed from by a user. When the lid section 9 is in the closed position, a cartridge 100 inserted into the channel 8 is held within the apparatus 1 against the heater 13.

The apparatus 1 may further comprise one or more air inlets, in this example air inlet 7e formed through the section 7b, to allow air to flow into the housing 3 when a user draws on the mouthpiece 11.

In this example, the heater 13 comprises a thin elongate heating plate comprising a pair of opposite surfaces or faces (only one of which 13a is visible in the Figures). The heating plate may be formed of a heat conducting material, for example, a metal such as alumina. The heater 13 is arranged with its longitudinal axis parallel with that of the apparatus 1 with a first of the surfaces 13a exposed and a second of the surfaces resting flush against the support platform 7a. The exposed surface 13a may be curved, for example, convex or concave, and in this example, the exposed surface 13a is convex in shape. The heater 13 comprises a resistive heating element, for example circuitry (not shown) formed e.g. printed on the exposed surface 13a.

The apparatus 1 further has an electronics/power chamber, within the main housing 5, which in this example contains a power source 19 and electrical control circuitry 21. The electrical control circuitry 21 may include a controller, such as a microprocessor arrangement, configured and arranged to control the heater 13 as discussed further below.

The power source 19 may be a battery, which may be a rechargeable battery or a non-rechargeable battery. Examples include nickel cadmium batteries although any suitable batteries may be used. The battery 19 is electrically coupled to the heater 13 to supply electrical power when required and under control of the electrical control circuitry 21 to heat the aerosol generating material in the cartridge 100 (as discussed, to volatilize the aerosol generating material without causing the aerosol generating material to combust or undergo pyrolysis). The apparatus 1 further comprises a charging slot 5c (see FIG. 3), in this example formed through the first end 5a of the main housing section 5 to allow a charger (not shown) to be electrically connected to the battery 19 if the battery 19 is a rechargeable battery or to connect an external device (e.g. a computer) to the control circuitry 21 to download data from the control circuitry or upload data or software to the control circuitry 21.

The apparatus 1 may further comprise one or other or both of a manual actuator (not shown in the Figures) for example, a push button, and a control sensor (not shown in the Figures), for example an airflow sensor, each operably coupled to the control circuitry 21. A user may manually operate the heater 13 or the heater 13 can be operated automatically in response to the sensor detecting a user drawing on the mouthpiece 11.

Figure 6:
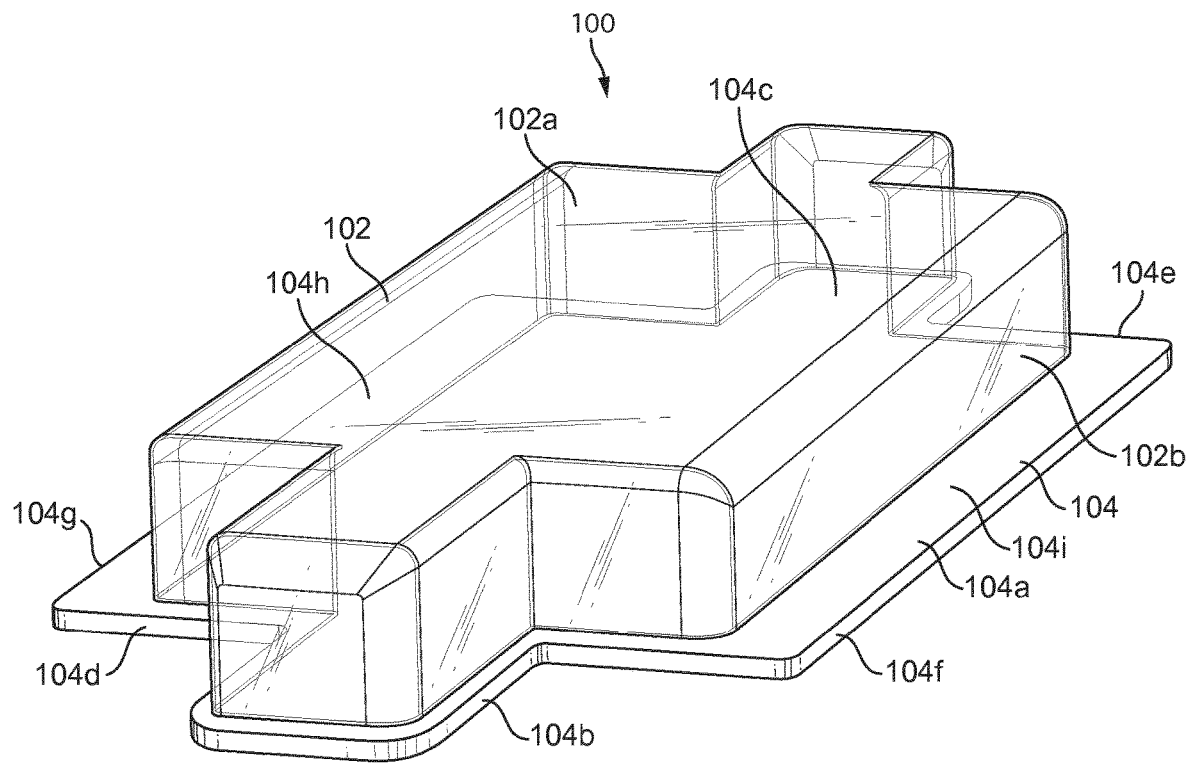
FIG. 6 shows a schematic perspective view of the first example of the cartridge.
Figure 7:
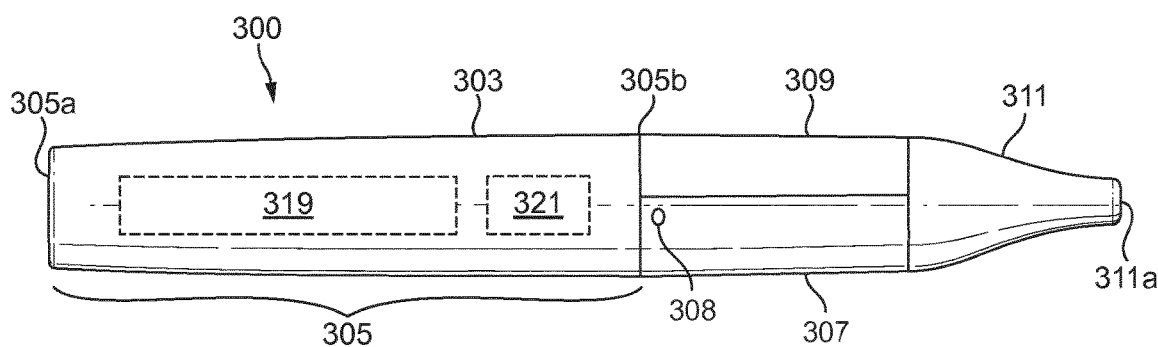
FIG. 7 shows a schematic side view of a second example of an apparatus for heating an aerosol generating material.
Figure 8:
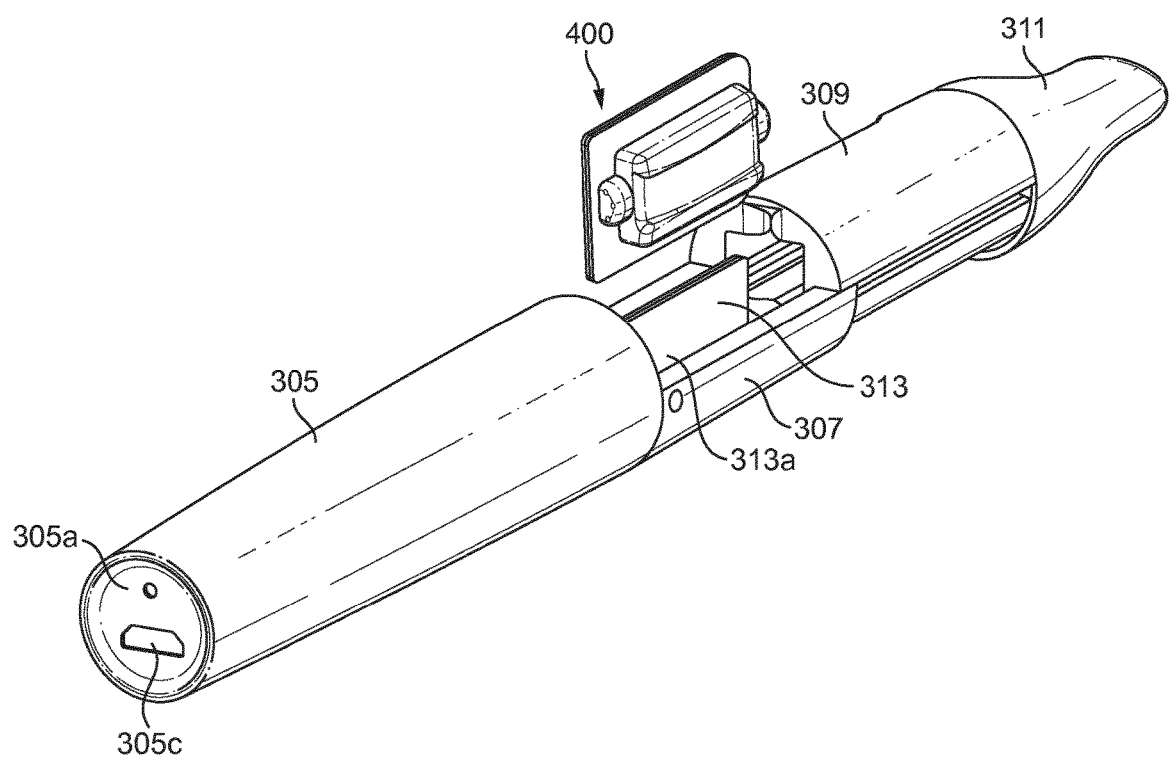
FIG. 8 shows a schematic perspective of the apparatus of FIG. 7 with a lid section in an open position and a second example of a cartridge being inserted into the apparatus.
Figure 9:
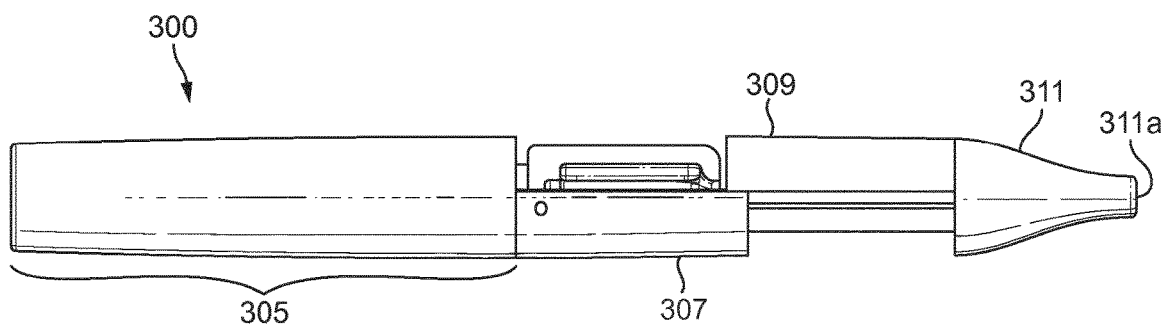
FIG. 9 shows a schematic side view of the apparatus of FIG. 7 with the lid section in the open position and the second example of a cartridge inserted into the apparatus.

Referring now to FIG. 6, in particular, the cartridge 100 comprises a protective cover 102 attached to, for example adhered to, a planar base 104. The cover 102 and the planar base 104 together form a first body that defines a chamber for containing the aerosol generating material (not shown). The base 104 is substantially parallel to a longitudinal axis of the first body.

In this example, the planar base 104 comprises a main rectangular section 104a and identical first 104b and second 104c projections that project from respective opposite first 104d and second 104e sides of the main rectangular section 104a. The area of the first 104b and second 104c projections is relatively small compared to that of the main rectangular section 104a. The first 104b and second 104c projections are opposite each other and are arranged symmetrically about the longitudinal axis of the planar base 104.

The protective cover 102 comprises a top surface 102a and a multi-faceted side surface 102b. The footprint of the protective cover 102 covers most of the planar base 104. In this example, the protective cover 102 covers substantially all of the first 104b and second 104c projections and most of the main rectangular section 104a. First 104h and second 104i relatively narrows strips of the main rectangular section 104a along third 104f and fourth 104g sides of the main rectangular section 104a are not covered by the protective cover 102.

The planar base 104 is formed of a sheet of thermally conductive material, for example, metal foil such as aluminum foil.

The protective cover 102 is formed of a plastic material, typically a thermoformed plastic material such as PVC or an Orientated Polyamide (OPA). In one example, the protective cover is multi-layered comprising an outer plastic material layer (e.g. an OPA) and an inner foil layer (e.g. aluminum foil).

The protective cover 102 is adhered to the planar base 104 using a suitable adhesive.

In the multi-layered example described above, for example, the protective cover 102 is bonded to the planar base 104 by way of a layer of bonding lacquer, such as a high heat resistant lacquer that is underneath the inner foil layer. Advantageously, using a high heat resistant lacquer enables rapid heating at high temperatures. In some embodiments, the bonding lacquer is only provided in regions where the protective cover 102 contacts the planar base 104 and is applied only on one or other of the protective cover 102 and the planar base 104. This minimizes the amount of heat resistant lacquer used and makes it less likely that, in use, heating causes the lacquer to volatilize. In one example, the adhesive may be applied to the areas in which there is no aerosol generating material.

Figure 3:
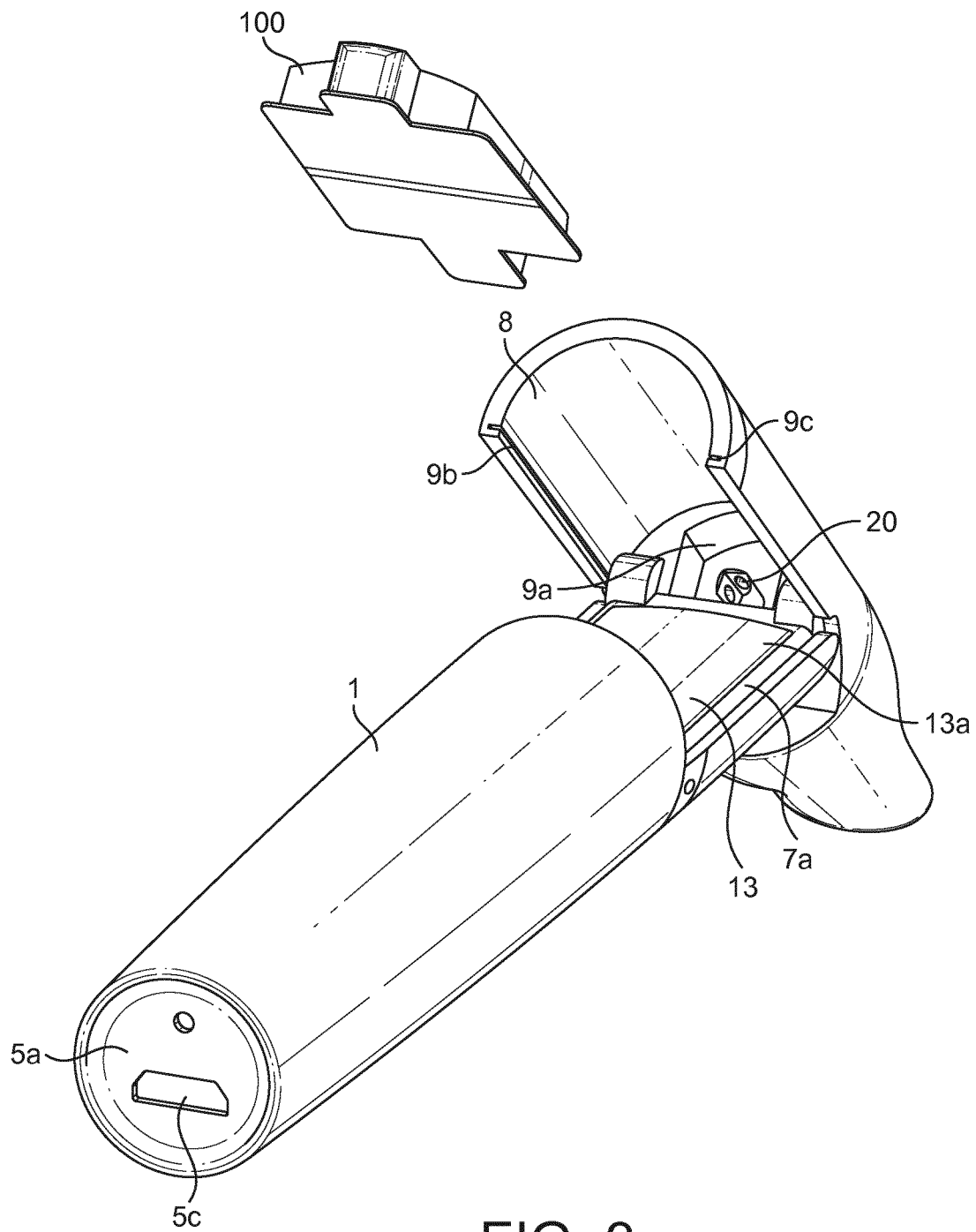
FIG. 3 shows a schematic perspective of the apparatus of FIG. 1 with the lid section in an open position and a first example of a cartridge being inserted into the apparatus.
Figure 4:
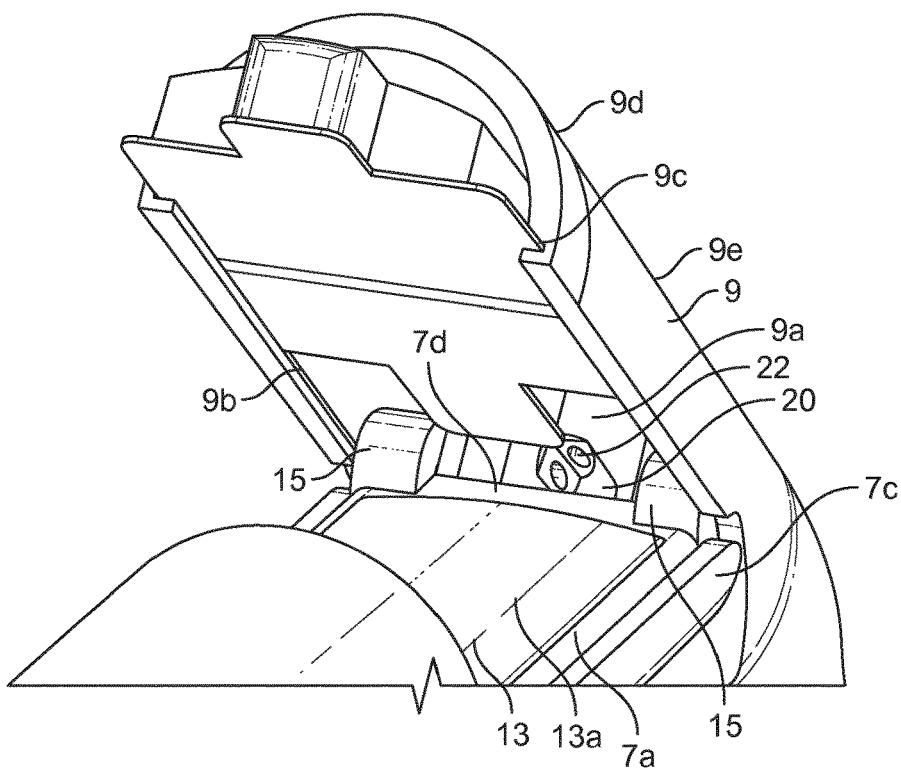
FIG. 4 shows an expanded schematic perspective view of a part of the apparatus of FIG. 1 with the first example of a cartridge being inserted into the apparatus.
Figure 5:
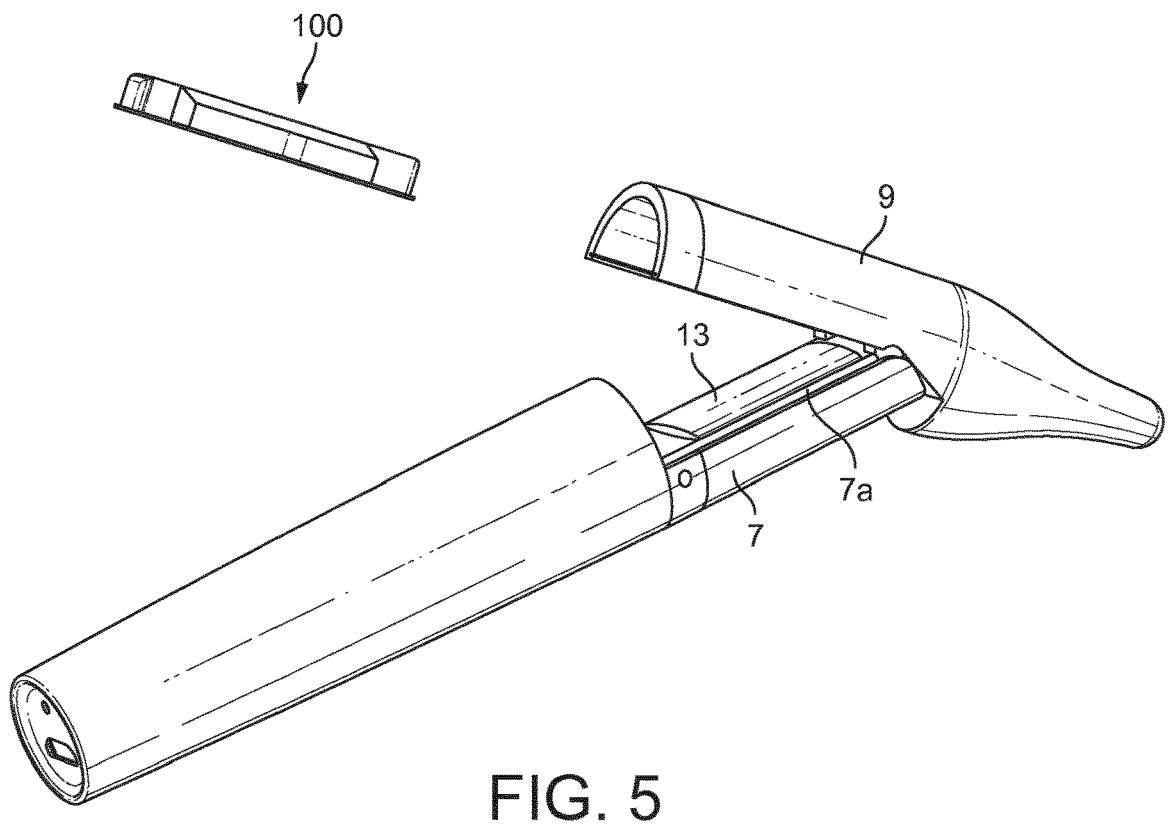
FIG. 5 shows a further schematic perspective of the apparatus of FIG. 1 with the lid section in an open position.

As perhaps is best seen in FIGS. 3 and 4, the lid section 9 of the apparatus 1 comprises a pair of spaced apart parallel guide slots 9b, 9c formed in an inner surface of the lid section 9. One of the guide slots 9b is formed close to and runs along a first straight edge of the lid section 9 and the other of the guide slots 9c is formed close to and runs along a second straight edge of the lid section 9 that is opposite the first straight edge.

In order to insert the cartridge 100 into the lid section 9, a user aligns the third side 104f of the main rectangular section 104a with the guide slot 9c and aligns the fourth side 104g of the main rectangular section 104a with the guide slot 9b (see FIG. 3) and pushes the cartridge 100 into an inserted position in the open channel 8. When the cartridge 100 is in the inserted position (FIG. 4 shows the cartridge partially in the inserted position), the third 104f and fourth 104g sides of the cartridge 100 are supported in the guide slots 9c, 9b.

As best seen in FIGS. 3 and 4, the lid section 9 further comprises an inner end face 9a that comprises a first protrusion 20 that extends into the inside of the lid section 9. When the cartridge 100 is inserted into the lid section 9, the first protrusion 20 which has a sharp or pointed end, pierces a leading face of the protective cover 102.

Figure 2:
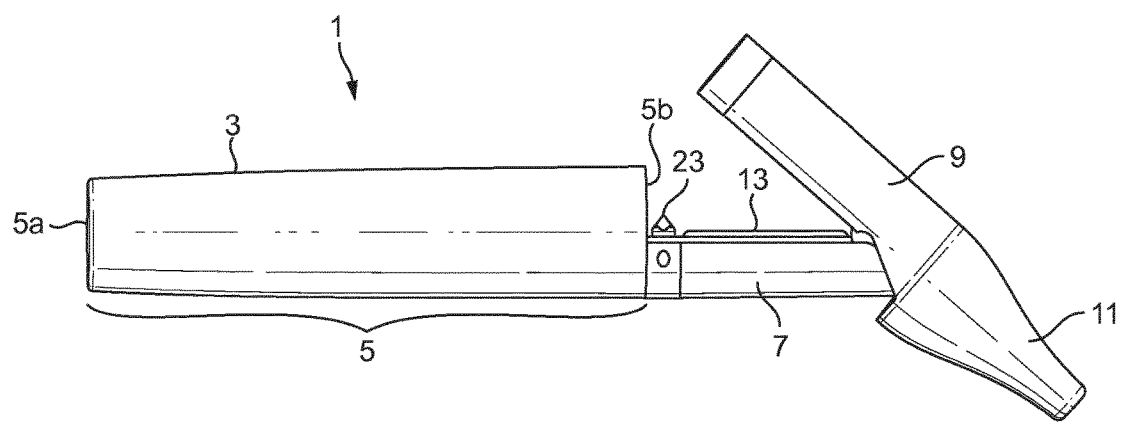
FIG. 2 shows a schematic side view of the apparatus of FIG. 1 with a lid section in an open position.

As best seen in FIG. 2, a second protrusion 23 is positioned on the heater support platform 7a at a location between the heater 13 and the main housing section 5. The second protrusion 23 extends upwardly from the heating support platform 7a.

When a user moves the lid section 9 from the open position to the closed position and a cartridge 100 is inserted, the second protrusion 23 which has a sharp or pointed end is brought into contact with and pierces the first projection 104b of the planar base 104.

The closed lid section 9 effectively 'clamps' the inserted cartridge 100 against the first surface 13a of the heater 13 with at least a major portion or all of the bottom surface of the planar base 104 in contact with the first heating surface 13a. When held in position in this way, the planar base 104, which is flexible, deforms or curves slightly to adopt the convex shape of the heating surface 13a. This arrangement provides for a particularly good thermal contact between the first heating surface 13a and the planar base 104.

The first protrusion 20 comprises one or more air passageways formed there through which are in fluid communication with the outlet 11a of the mouthpiece 11. Similarly, the second protrusion 23 comprises one or more air passageways formed there through which are in fluid communication with the one or more air inlets 7e formed in the housing 3. Accordingly, the first protrusion 20 acts as an outlet of the cartridge 100 and the second protrusion 23 acts as an inlet of the cartridge 100.

In use, when a user actuates the actuator (not shown), the control circuitry 21 is operated so that electrical current flows through the resistive heating element (not shown) formed on the first heating surface 13a causing the heater 13 to heat up. As mentioned above, the base 104 is made of a thermally conductive material and is in good thermal contact with the first heating surface 13a. There is therefore a very efficient transfer of heat from the heating 13 to the interior of the cartridge 100 whereby the aerosol generating material in the cartridge 100 is heated. This causes at least one component of the aerosol generating material to volatilize without combusting the aerosol generating material. Advantageously, because the planar base 104 is substantially parallel to the longitudinal axis of the first body defined by the cover 102 and the planar base 104, the aerosol generating material in the cartridge 100 can be heated efficiently and uniformly along substantially the entire length of the cartridge 100.

When the user draws on the mouthpiece 11, this causes a reduction in pressure in the cartridge 100, which causes airflow to be drawn into the housing 3 through the one or more inlets 7e and airflow to be drawn into the cartridge 100 via the air passageway holes in the second protrusion 23. Typically, this airflow into the cartridge 100 causes the volatilized component(s) of the aerosol generating material 43 to be cooled, so that it/they condense(s) to form an aerosol.

The user's continued drawing causes the airflow and aerosol to be drawn into the user's mouth via the mouthpiece 11. This can be repeated until the volatile component(s) is/are exhausted. In some examples, the volatilized component(s) of the aerosol generating material cool to form the aerosol within the cartridge 100 itself and in other examples the volatilized component(s) of the aerosol generating material cool to form the aerosol in the mouthpiece 11 after having exited the cartridge 100 via the air passageways in the first protrusion 20. In yet further examples, some of the aerosol is formed within the cartridge 100 and some of the aerosol is formed outside of the cartridge 100 in the mouthpiece 11.

When all, or substantially all, of the volatile component(s) of the aerosol generating material in the cartridge 100 has/have been spent, the user opens the lid section 9, removes the cartridge 100 and inserts another unspent cartridge 100 into the channel and repeats the above process.

Referring now to FIGS. 7 to 14, there is shown a second example of an apparatus 300 and a cartridge 400 that is insertable within the apparatus 300. Like the apparatus 1 described above, the apparatus 300 is a so-called "tobacco-heating-product" apparatus and is arranged to heat aerosol generating material (not shown) contained within the cartridge 400, when the cartridge 400 is inserted inside the apparatus 300 to volatilize at least one component of the aerosol generating material.

The apparatus 300 in this second example is again generally elongate and comprises a generally tubular housing 303. A shown in FIGS. 7, 8 and 9 in particular, the tubular housing 303 comprises a main housing section 305, a heater support section 307 connected to the main housing section 305, a lid section 309 connected to the heater support section 307 and a mouth piece 311 connected to the lid section 309. The mouthpiece 311 comprises an outlet 311a.

The main housing section 305 comprises first 305a and second 305b longitudinal ends. The first end 305a defines a distal end of the whole of the apparatus 300 and the second end 305b is located at approximately just over half of the way along the length of the apparatus 300.

The heater support section 307 extends from the second 305b longitudinal end of the main housing section 305 and defines a platform that supports a heater 313. The lid section 309 is slidably connected to the heater support section 307 so that it can be slid between a closed position shown in FIG. 7, in which the heater 313 is enclosed in the apparatus 300 and an open position shown in FIGS. 8 and 9 in which the heater 313 is exposed and in which a cartridge 400 can be inserted into the apparatus 300, as will be described in more detail below.

The apparatus 300 may further comprise one or more air inlets 308, which in this example, are formed through the section 307 and which is/are in fluid communication with the outlet 311a of the mouthpiece 311.

The apparatus 300 and its various sections may comprise any of the materials described above with respect to the first example.

In this example, a heater 313 is in the form of a thin elongate plate comprising a pair of opposite first and second heating surfaces 313a or faces (only one of which is visible in the Figures). The heater 313 is arranged with its longitudinal axis parallel with that of the apparatus 300 and is supported in the heater support section 307 upright along one of its long edges so that both of the opposite first and second heating surfaces or faces 313a are exposed in the heater support section 307. Similarly to the heating surface 13a discussed above, each of the first and second heating surfaces 313a may also be curved, for example concave or convex in shape and may have formed thereon, e.g. printed, a respective resistive heating element, for example circuitry (not shown).

Similarly to the apparatus 1 described above, the apparatus 300 further has an electronics/power chamber, within the main housing section 305, which in this example contains a power source 319 and electrical control circuitry 321. Again, the electrical control circuitry 321 may include a controller, such as a microprocessor arrangement, configured and arranged to control the heater 313 as discussed further below.

The power source 319 may be any of the power sources described above in respect of the apparatus 1. Again, the power source 319 is electrically coupled to the heater 313 to supply electrical power when required and under control of the electrical control circuitry 321 to heat the aerosol generating material in the cartridge 400 (as discussed, to volatize the aerosol generating material without causing the aerosol generating material to combust or undergo pyrolysis). Again, the apparatus 300 further comprises a charging slot 305c, which in this example, is formed through the first end 305a of the main housing section 305 to allow a charger (not shown) to be electrically connected to the power source 319 if the power source 319 is a rechargeable battery or to connect an external device (e.g. a computer) to the control circuitry 321 to download data from the control circuitry or upload data or software to the control circuitry 321.

The apparatus 300 may further comprise any of the actuators and/or sensors as described above with respect to the apparatus 1 operably coupled to the control circuitry 321.

As best seen in FIG. 10a to FIG. 10d, in this example, the cartridge 400 is a dual-body arrangement comprising a first cartridge body 400a and a second cartridge body 400b. Each of the first cartridge body 400a and the second cartridge body 400b comprises a respective protective cover 402, 402' attached to, for example adhered to a respective planar base 404, 404'. Each cover 402, 402' and the planar base 404, 404' it is attached to together define a chamber for containing the aerosol generating material (not shown). The planar base 404 is substantially parallel to the longitudinal axis of the first cartridge body 400a and the planar base 404' is substantially parallel to the longitudinal axis of the second cartridge body 400b.

In this example, each planar base 404, 404' is substantially rectangular in shape although other shapes are possible. Each protective cover 402, 402' comprises a main elongate central section 402a, 402a' and smaller first 402b, 402b' and second 402c, 402'c end sections at respective ends of the main elongate central section 402a, 402a'. As best appreciated from FIG. 10a, the second 402c, 402'c end sections are offset with respect to each other about the longitudinal axis of the cartridge 400. Each central cover section 402a, 402a' defines an elongate recess 403, 403' along its upper surface.

Figure 10A:
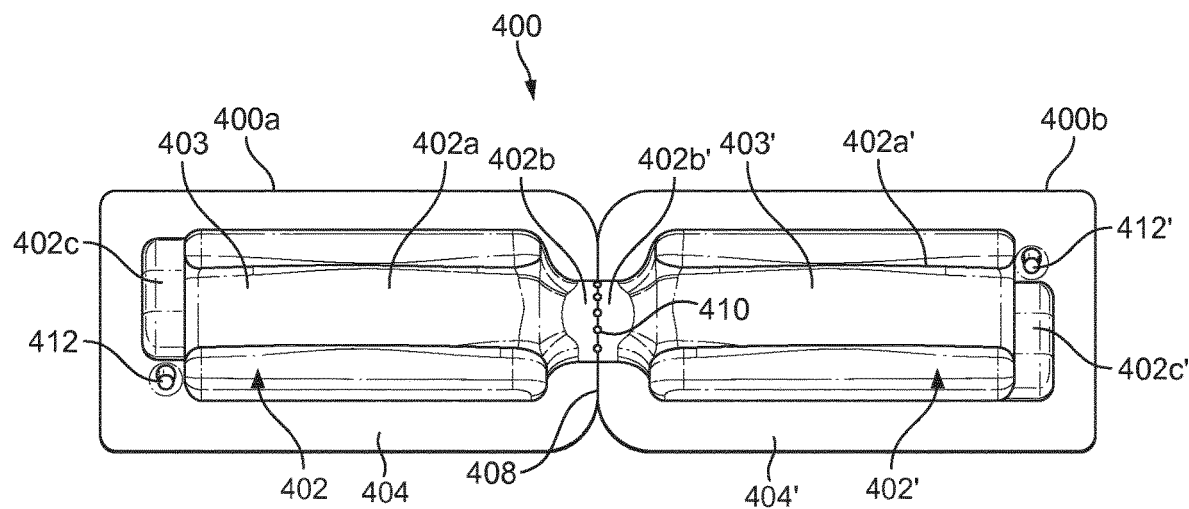
FIGS. 10a to 10d show the second example of a cartridge.

As is also best appreciated from FIG. 10a, the planar bases 404, 404' are connected together at opposing ends along a first line of weakening 408 and the first 402b, 402b' end sections are also connected together at opposing ends along a second line of weakening 410 that is aligned with the first line of weakening 408. The lines of weakening may be for example a perforated line, a serrated line or a cut line.

As described above in respect of the cartridge 100, the planar bases 404, 404' are formed of a sheet thermally conductive material, for example, metal foil such as aluminum foil, and the protective covers 402, 402' may be formed any of the materials described above with respect to the first example and adhered to the planar bases 404, 404' using a suitable adhesive as also described above with respect to the first example.

Figure 10B:
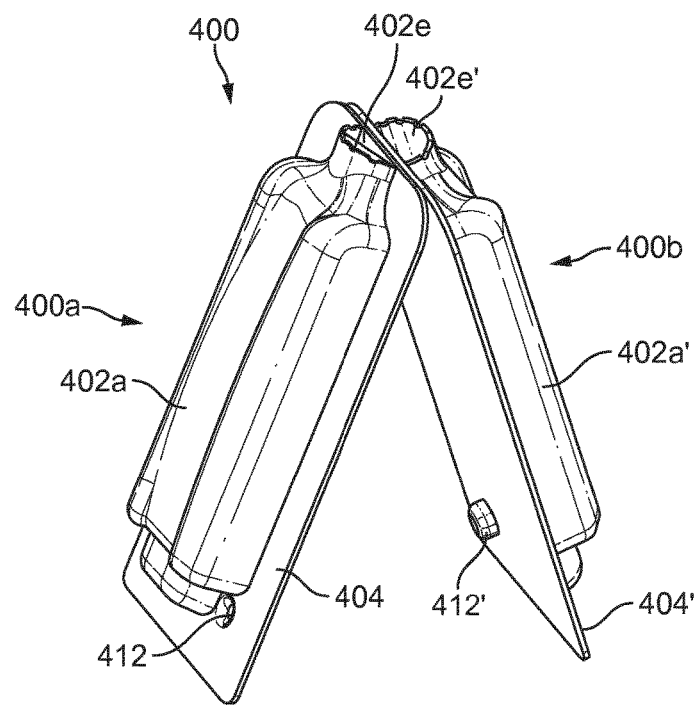

In order to insert a cartridge 400 into the apparatus 300, a user takes a cartridge 400 in a "prior to use" configuration shown in FIG. 10a and folds the planar bases 404, 404' towards one another about the first weakening line 408. The folding causes the first cartridge body 400a and the second cartridge body 400b to separate from one another about the second weakening line 410 exposing the interior of the first cartridge body 400a through the aperture 402e and exposing the interior of the second cartridge body 400b through the aperture 402e', as best shown in FIG. 10b. The aperture 402e provides an outlet for the first cartridge body 400a and the aperture 402e' provides an outlet for the second cartridge body 400b.

The user may then arrange the cartridge 400 in the interior of the heater support section 307 with the heater 313 between the planar bases 404, 404' and continue to fold the planar bases 404, 404' together until the heater 313 is sandwiched between them. In this position, at least a major portion or all of the bottom surface of the planar base 404 is against the first heating surface 313a of the heater 313 and at least a major portion or all of the bottom surface of the planar base 404' is against the second heating surface of the heater 313.

Each of the first cartridge body 400a and the second cartridge body 400b comprises a respective member 412, 412', which in this example is in the form of a short tube that is open at both of its ends and extends through a planar base 404, 404' defining a passage through that planar base 404, 404' from one side to the other. Each member 412, 412' is located outside of a cover 402, 402' but directly adjacent to a central section 402a, 402a and a second end section 402, 402'. Each member 412, 412' protrudes away from the underside of the planar base 404, 404' that it extends through.

Figure 10C:
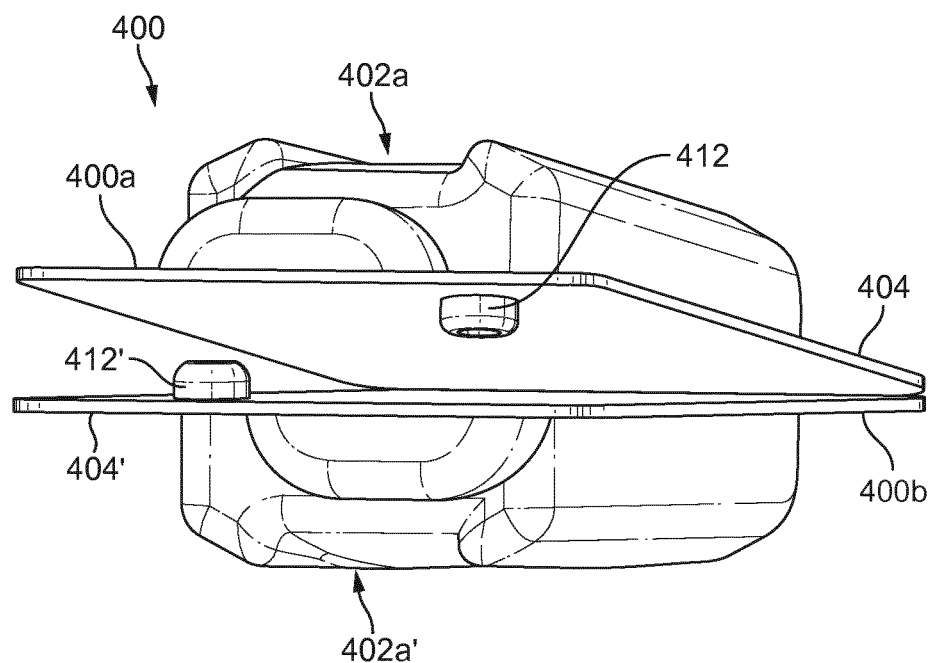
Figure 10D:
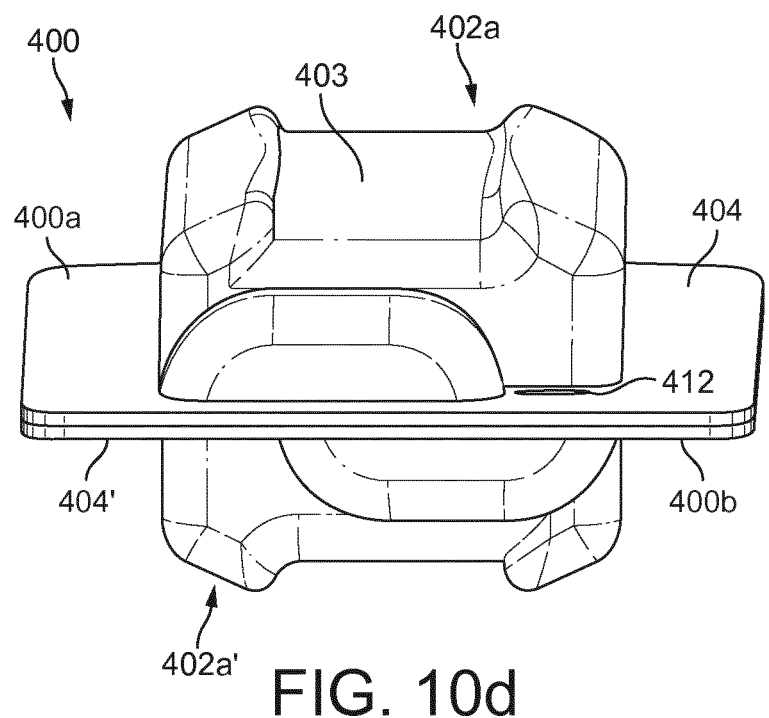

As is best appreciated from FIGS. 10c and 10d (which for clarity do not illustrate the heater 313), when the planar bases 404, 404' are folded so that the heater 313 is sandwiched between them, the member 412' punctures through the planar base 404 of the first cartridge body 400a in a region beneath the second 402c end section of the cover 402 of the first cartridge body 400a. Likewise, the member 412 punctures through the planar base 404' of the second cartridge body 400b in a region beneath the second 402c' end section of the cover 402' of the second cartridge body 400b'. Accordingly, the ends of the members 412, 412' that puncture through the planar bases 404, 404' are preferably sharpened or pointed or the like in order to facilitate this puncturing. As will be explained in more detail below, the member 412 acts as an inlet for the second cartridge body 400b and the member 412' acts as an inlet for the first cartridge body 400a.

Figure 11A:
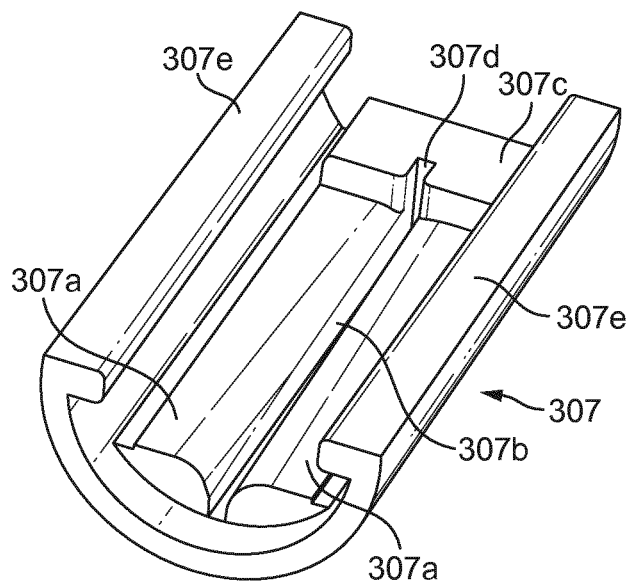
FIG. 11a shows a heater support section of a second example of an apparatus for heating an aerosol generating material.
Figure 12:
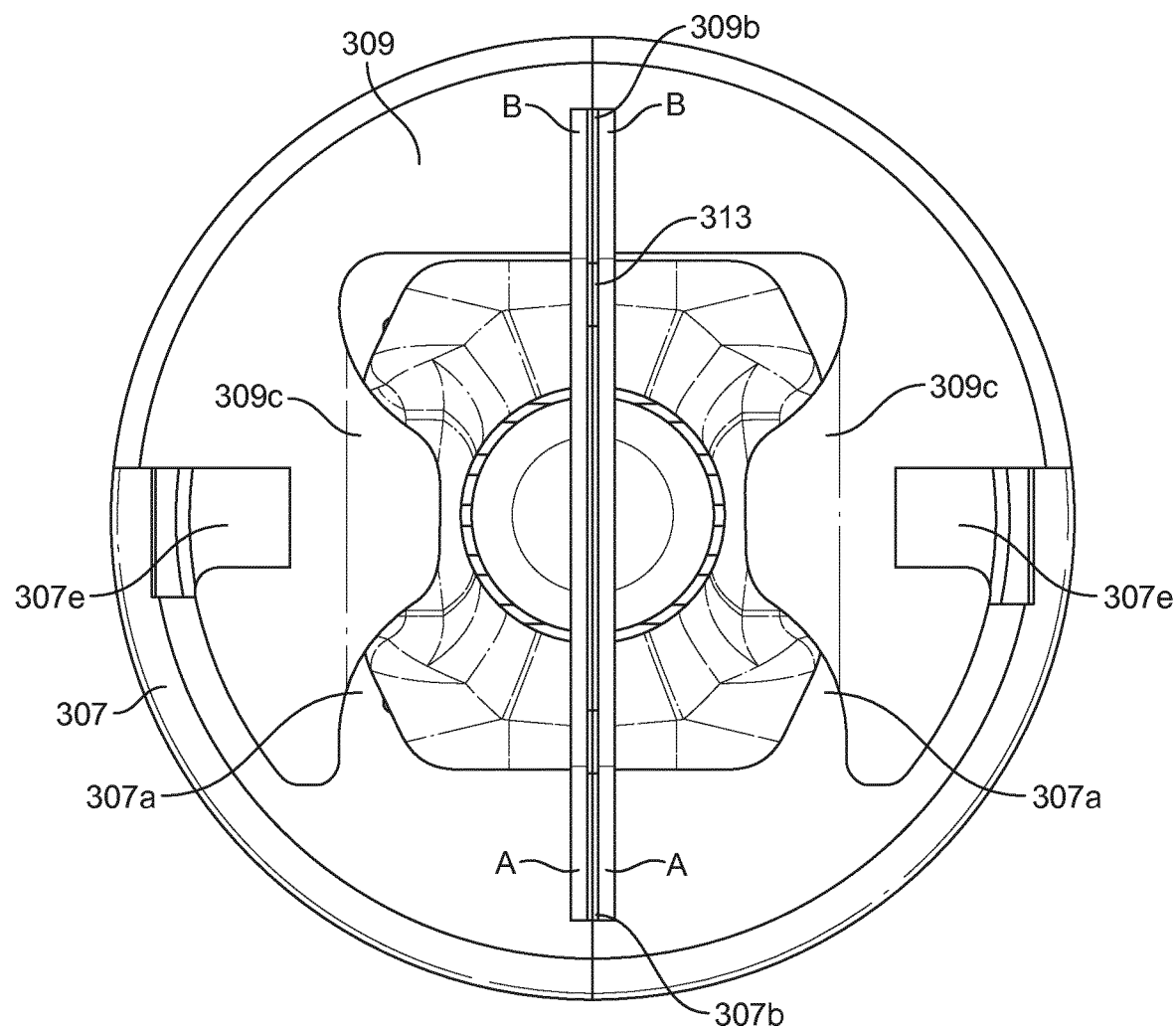
FIG. 12 shows a cross section through the heater support section and lid section of the second example of an apparatus when the second example of a cartridge is inserted in the second example of an apparatus.

As is best appreciated from FIGS. 11a and 12, the heater support section 307 is generally 'U' shaped in cross section and comprises a first pair of parallel ridges 307a that run along its base and which define between them a first longitudinal slot 307b. At one end, the pair of parallel ridges 307b terminate in a raised cross piece 307c that straddles the parallel ridges 307a and which defines a second slot 307d that runs into the first longitudinal slot 307a such that the first 307a and second 307d slots meet at an angle of about 90 degrees. The heater 313 is supported in the second slot 307d and sits with an edge running parallel to and just above the first longitudinal slot 307b. When a cartridge 400 is inserted in the apparatus 300, the cover end sections 402b, 402b' are supported on the cross piece 307c.

As shown in FIG. 12, when the cartridge 400 is positioned in the apparatus 300, respective first opposing sections (labeled "A") of the planar bases 404, 404' are received in the first longitudinal slot 307b and each of the main elongate central cover sections 402a, 402a' are supported on a respective one of the parallel ridges 307a.

Each of the parallel longitudinal edges 307e of the heater support section 307 defines a respective guide rail which extends slightly inwardly of the heater support section 307 and is used to slidably support the lid section 309.

Figure 11B:
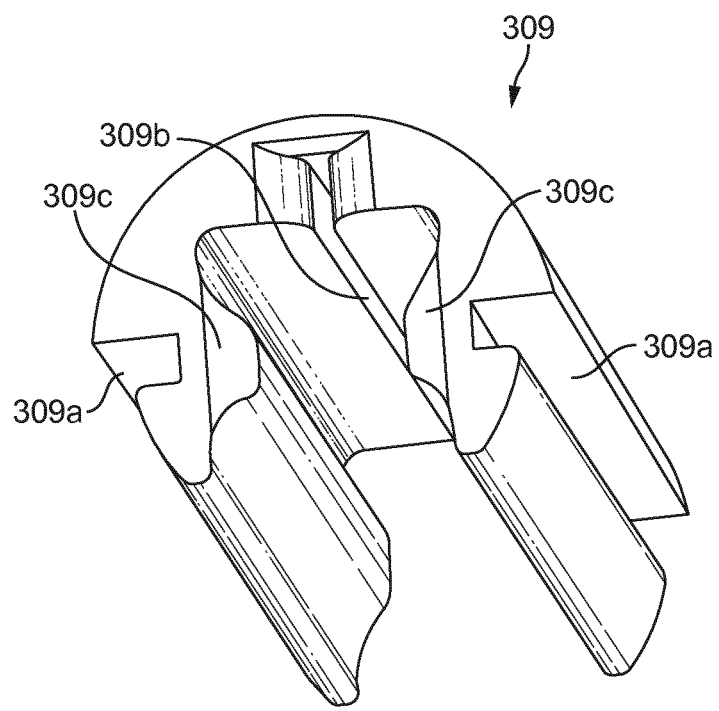
FIG. 11b shows a lid section of a second example of an apparatus for heating an aerosol generating material.

As is best appreciated from FIGS. 11b and 12, the lid section 309 is also substantially "U" shaped in cross section. The lid section 309 defines a pair of parallel longitudinal slots 309a arranged at corresponding positions on opposite sides of the exterior surface of the lid section 309. As is shown in FIG. 12, the lid section 309 is slidably mounted on the heater support section 307 by means of each of the guide rails 307e of the heater support section 307 being received in a respective one of the parallel longitudinal slots 309a of the lid section 309. This enables the lid section 309 to be slid between the open position shown in FIGS. 8, 9 and 13 in which a cartridge 400 can be inserted into or removed from the apparatus 300 and the closed position shown in FIG. 7 in which, if inserted, a cartridge 400 is enclosed in the apparatus 400.

The lid section 309, on its internal surface, defines a second longitudinal slot 309b which is parallel to and opposite the first longitudinal slot 307b in the heater support section 307. When the lid section 309 is in the closed position, the second longitudinal slot 309b receives respective second opposing sections (labeled "B") of the planar bases 404, 404', as is illustrated in FIG. 12. The lid section further defines, on its internal surface, a second pair 309c of parallel and opposing ridges. When the lid section 309 is in the closed position and a cartridge 400 is inserted in the apparatus 300, each of the second pair of ridges 309c is received in a respective recess 403, 403' defined in the main elongate central section 402a, 402a' of a protective cover 402, 402' of a respective one of the first 402a, 402b and second cartridge bodies.

Figure 13:
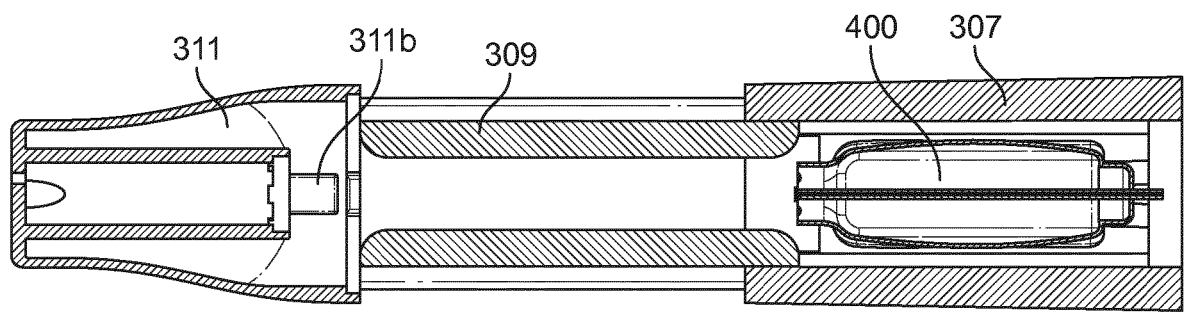
FIG. 13 shows a schematic cut away plan view of a part of the second example of an apparatus when the lid section is in the open position.
Figure 14:
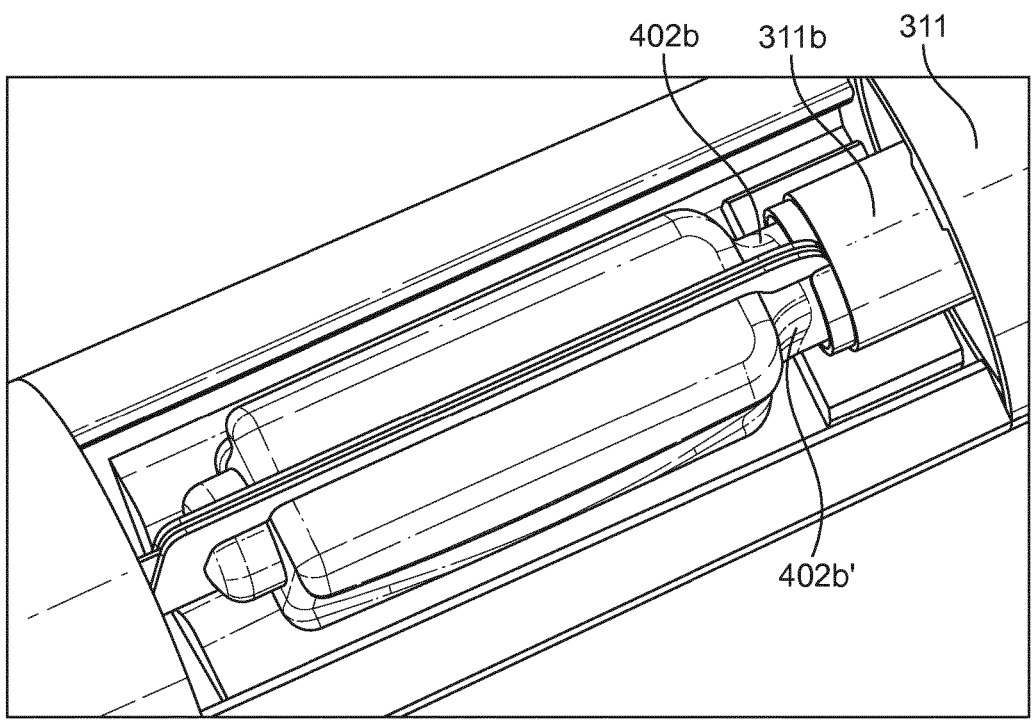
FIG. 14 shows a schematic cut away plan view of a part of the second example of an apparatus when the lid section is in the closed position.

As shown in FIGS. 13 and 14, the mouthpiece 311 comprise a gasket 311b that has a generally circular cross section, which is located at the end of the mouthpiece 311 which connects to the lid section 309. The gasket 311b, when the lid section 309 is moved into the closed position, engages the open end sections 402b, 402b' of the protective covers 402, 402'. The gasket 311b is in fluid communication with the outlet 311a of the mouthpiece 311.

In use, when a user actuates the actuator (not shown), the control circuitry 321 is operated so that electrical current flows through the resistive heating elements (not shown) formed on the first 313a and second heating surfaces to cause the heater 313 to heat up so that the first heater surface 313a heats the aerosol generating material in the first cartridge body 400a and the second heater surface heats the aerosol generating material in the second cartridge body 400b. Again, as the planar bases 404, 404' are formed of a thermally conductive material and are in good thermal contact with the heater 313, heat is very efficiently transferred to the aerosol generating material in each cartridge body 400a, 400b. This causes at least one component of the aerosol generating material in each cartridge body 400a, 400b to volatilize without combusting the aerosol generating material.

When the user draws on the mouthpiece 311, this causes a reduction in pressure in each cartridge body 400a, 400b, which causes air to be drawn into each cartridge body 400a, 400b via the air inlet 308 of the section 307 and the respective air inlets defined by the members 412' and 412. Typically, this airflow causes the volatilized component(s) of the aerosol generating material to be cooled, so that it/they condense to form an aerosol either inside each cartridge body 400a, 400b, inside the mouthpiece 311 or inside both. The user's continued drawing causes the airflow and aerosol to be drawn into the user's mouth via the mouthpiece 311. This can be repeated until the volatile component(s) is/are exhausted. The airflow and volatilized component(s) of the aerosol generating material and/or aerosol exit the cartridge bodies 400a, 400b through the apertures 402e, 402e'.

When all, or substantially all, of the volatile component(s) of the aerosol generating material in the cartridge 400 has/have been spent, the user opens the lid section 309, removes the cartridge 400 and inserts another unspent cartridge 400 into the channel and repeats the above process.

In some examples, the resistive heating elements (not shown) formed on the first 313a and second heating surfaces can be controlled independently of each other so that the aerosol generating material in each cartridge body 400a, 400b can be heated independently of each other in different time intervals. The aerosol generating material may be different in each cartridge body 400a, 400b. For example, one of the cartridge bodies 400a, 400b may comprise a flavored material (e.g. menthol) and the user may use the actuator (not shown) in such a way that the control circuitry 321 only activates the resistive heating element (not shown) on the one of the first and second heating surfaces contacting the planar base 404, 404' of the particular cartridge body 400a, 400b containing the flavored material at times when the user would like to taste the flavor. In examples where the resistive heating elements (not shown) formed on the first 313a and second heating surfaces can be controlled independently of each other, the heater 313 may comprises a heat insulating layer (not shown) between, e.g. midway between, the first 313a and second heating surfaces to inhibit heat generated by an activated one of the resistive heating elements (not shown) being transferred through the body of the heater 313 to the heating surface on which the other non-activated one of the resistive heating elements is provided.

It will be appreciated that a cartridge 400 may be provided in a pack (not shown) of such cartridges with any side of any given planar base being connected to any side of any other given planar base by a line of weakening to enable a cartridge to be separated (i.e. broken away from) by a user from the pack of cartridges.

In a variation of the cartridge 400 (not illustrated), the first cartridge body 400a and the second cartridge body 400b are essentially mirror images of each other and so the second 402c, 402'c end sections are not offset with respect to each other about the longitudinal axis of the cartridge 400 but instead the second 402c, 402'c end sections are aligned and the respective members 412, 412' are aligned (e.g. the positions of the first end section 402c and the member 412 are reversed so that they mirror the positions of the of the first end section 402'c and the member 412', respectively).

In this example, a cartridge 400 in a pack of such cartridges may be broken away from the pack by pivoting long sides of the bases 404, 404' about lines of weakening connecting those long sides of the bases 404, 404' to corresponding long sides of the bases of another such cartridge in the pack. In this way, the member 412 will puncture through the first planar base of the first cartridge body of the other such cartridge remaining on the pack in a region beneath the second end section of the cover of the first cartridge body of that other such cartridge and likewise the corresponding member of the first cartridge body of that other such cartridge will puncture through the first planar base 404 of the first cartridge body 400a in a region beneath the second end section 402c of the cover 402. Similarly, the member 412' will puncture through the second planar base of the second cartridge body of the other such cartridge remaining on the pack in a region beneath the second end section of the cover of the second cartridge body of that cartridge and likewise the corresponding member of the second cartridge body of the other such cartridge will puncture through the second planar base 404' of the second cartridge body 400a' in a region beneath the second end section 402c' of the cover 402'. Once free of the pack, a user may then fold the planar bases 404, 404' towards one another about the first weakening line 408 to cause the first cartridge body 400a and the second cartridge body 400b to separate from one another about the second weakening line 410 similarly as discussed above with respect to FIGS. 10a and 10b.

Referring now to FIGS. 15 to 19b, there is shown a third example of an apparatus 500 and a cartridge 600 that is insertable within the apparatus 500. The apparatus 500 is similar to the apparatuses 1 and 300 described above and is another "tobacco-heating-product" apparatus arranged to heat aerosol generating material (not shown) contained within the cartridge 600 when the cartridge 600 is inserted inside the apparatus 500 to volatilize at least one component of the aerosol generating material.

Figure 15:
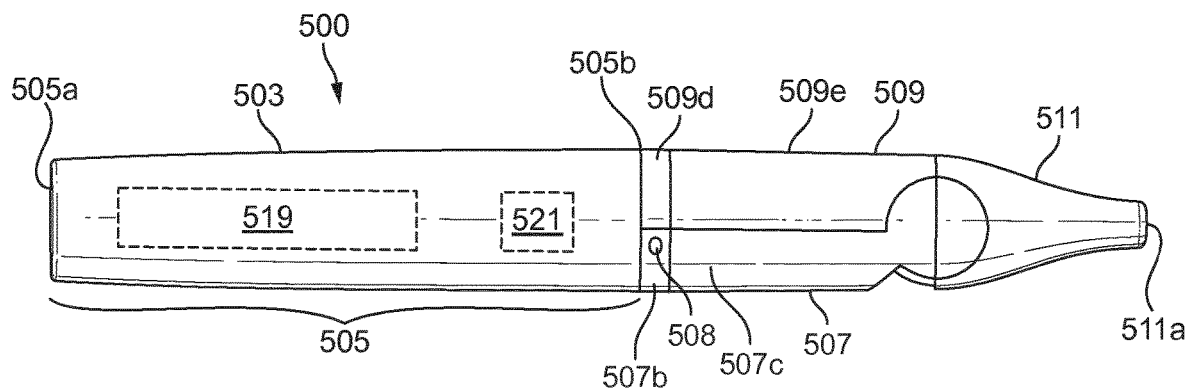
FIG. 15 shows a schematic side view of a third example of an apparatus for heating an aerosol generating material.
Figure 16:
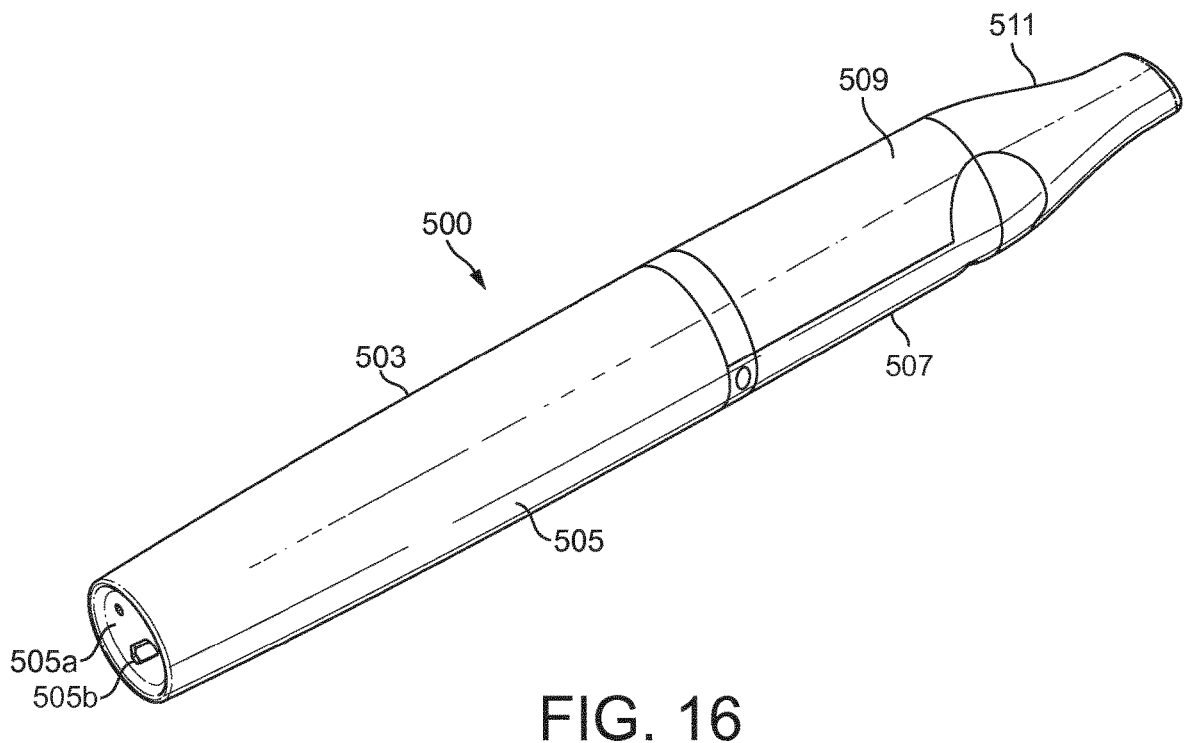
FIG. 16 shows a schematic perspective view of the third example of an apparatus for heating an aerosol generating material.
Figure 17:
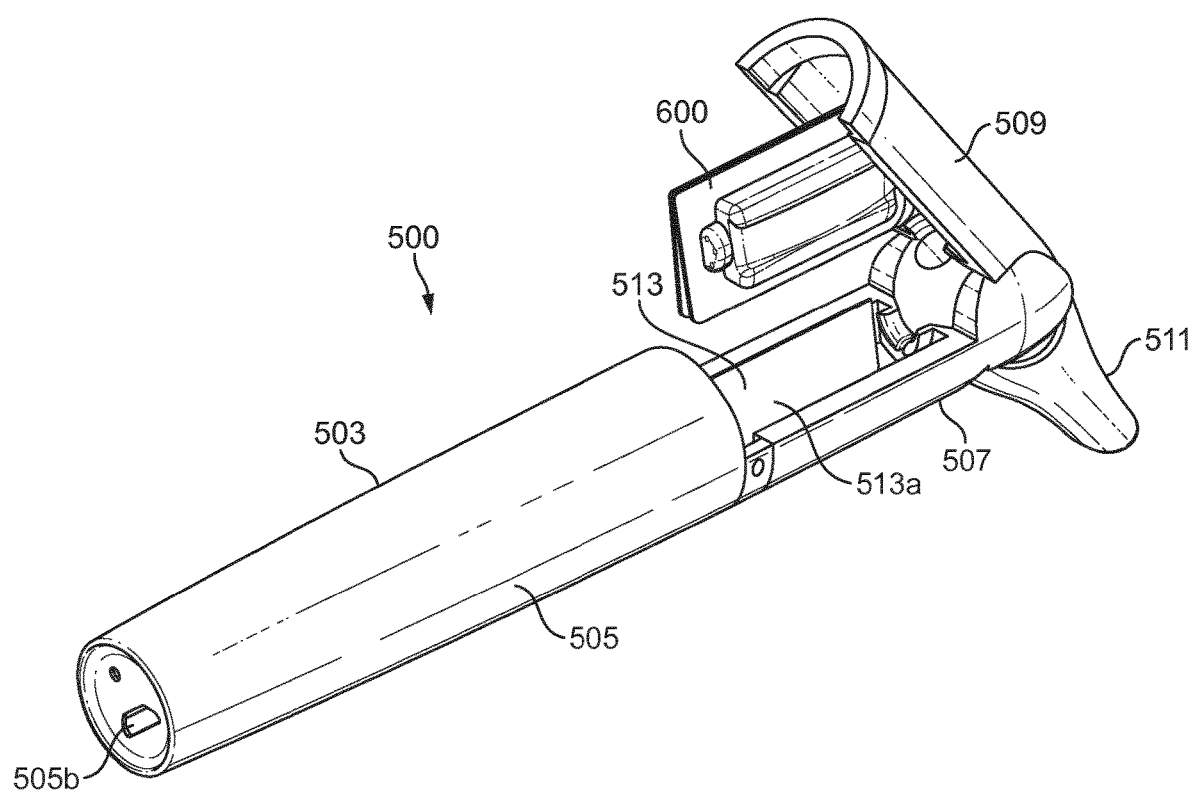
FIG. 17 shows a schematic perspective view of the third example of an apparatus for heating an aerosol generating material with a third example of a cartridge being inserted into the apparatus.

The apparatus 500 in this third example is again generally elongate and comprises a generally tubular housing 503. As shown in FIGS. 15, 16 and 17 in particular, the tubular housing 503 comprises a main housing section 505, a heater support section 507 that supports a heater 513, a lid section 509 and a mouth piece 511.

The main housing section 505 is very similar to the main housing sections of the two examples described above, and comprises a first longitudinal end 505a (which again defines a distal end of the whole of the apparatus 500) and a second longitudinal end 505b located at approximately just over half of the way along the length of the apparatus 500.

The heater support section 507 extends from the second 505b longitudinal end of the main housing section 505 and defines a platform that supports a heater 513. The heater support section 507 may, as is the case in this example, comprise a plurality 507b, 507c of interconnected sections, one of which 507b is connected to the main housing section 505, or the heater support section 507 may be a single piece section.

The apparatus 500 further comprises one or more air inlets 508, which in this example, are formed through the section 507c and which are in fluid communication with an outlet 511a of the mouthpiece 511.

The heater support section 507 and the lid section 509 are connected by a hinge arrangement that is arranged to enable the lid section 509 to pivot with respect to the heater support section 507, between a closed position shown in FIGS. 15 and 16 and an open position shown in FIG. 17. The lid section 509 may, as is the case in this example, comprise a plurality 509d, 509e of interconnected sections, one of which 509e is connected to the mouthpiece 511, or the lid section 509 may be a single piece section.

In this example, a heater 513, is similar to the heater in the second example, in that it is in the form of a thin elongate plate comprising a pair of opposite first and second heating surfaces 513a or faces (only one of which is visible) and is arranged with its longitudinal axis parallel with that of the apparatus 500 and is supported in the heater support section 507 upright along one of its long edges so that both of the opposite surfaces or faces 513a are exposed in the heater support section 507. Again, each of the first and second heating surfaces 513a may also be curved, for example concave or convex in shape and may have formed thereon, e.g. printed, a respective resistive heating element, for example circuitry (not shown).

As with the two examples described above, an electronics/power chamber, is provided within the main housing 505 containing a power source 519 (which may be any of the power sources described above) and electrical control circuitry 521 (which may comprise any of the control circuitry components described above) configured and arranged to control the heater 513. Yet again, the apparatus 500 further comprises a charging slot 505b, which in this example, is formed through the first end 505a of the main housing section 505 to allow a charger (not shown) to be electrically connected to the power source 519 if the power source 519 is a rechargeable battery or to connect an external device (e.g. a computer) to the control circuitry 521 to download data from the control circuitry or upload data or software to the control circuitry 521.

The apparatus 500 may further comprise any of the actuators and/or sensors as described above with respect to the apparatus operably coupled to the control circuitry 515.

Figure 18A:
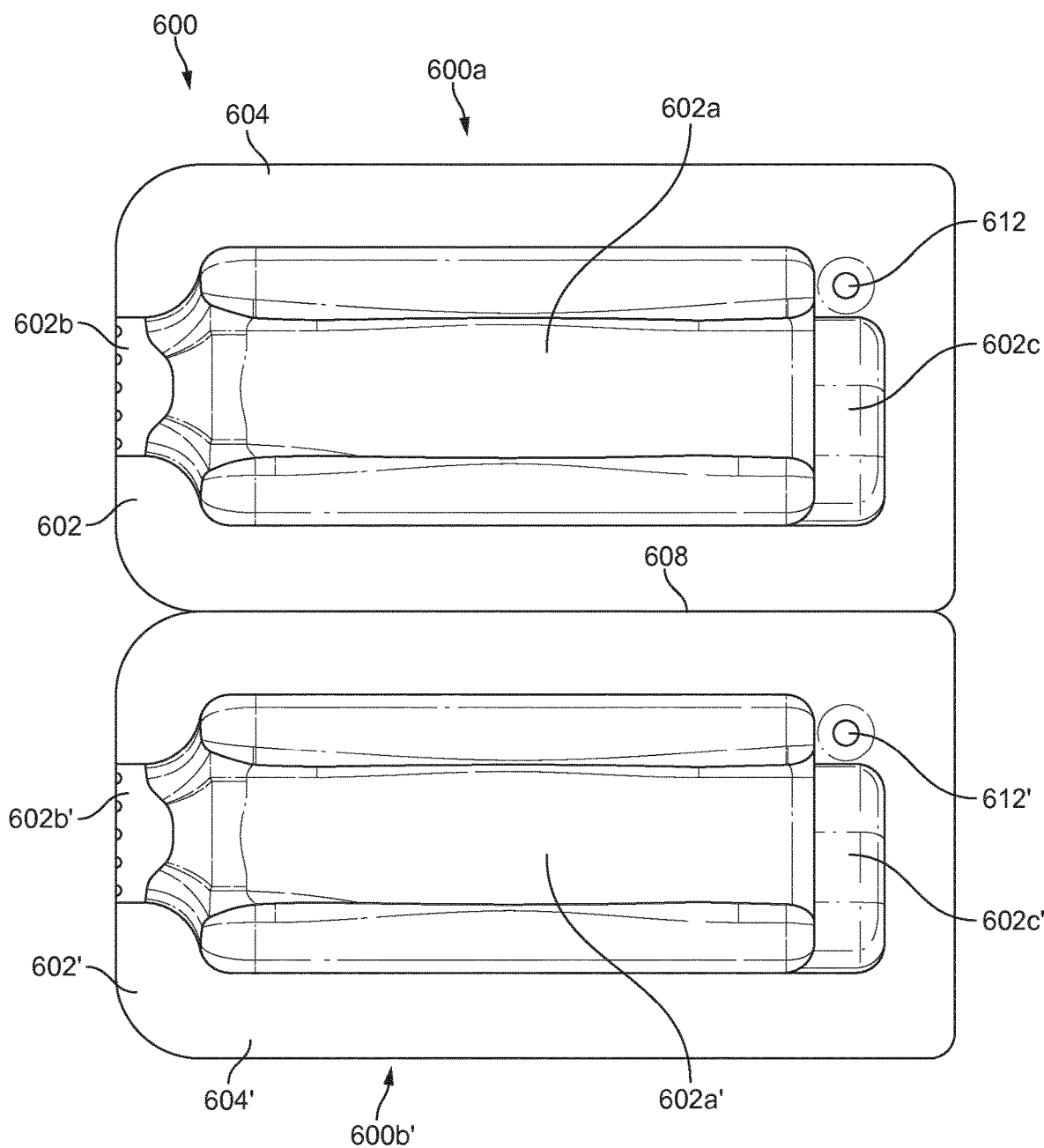
FIGS. 18a to 18c show the third example of a cartridge.
Figure 18B:
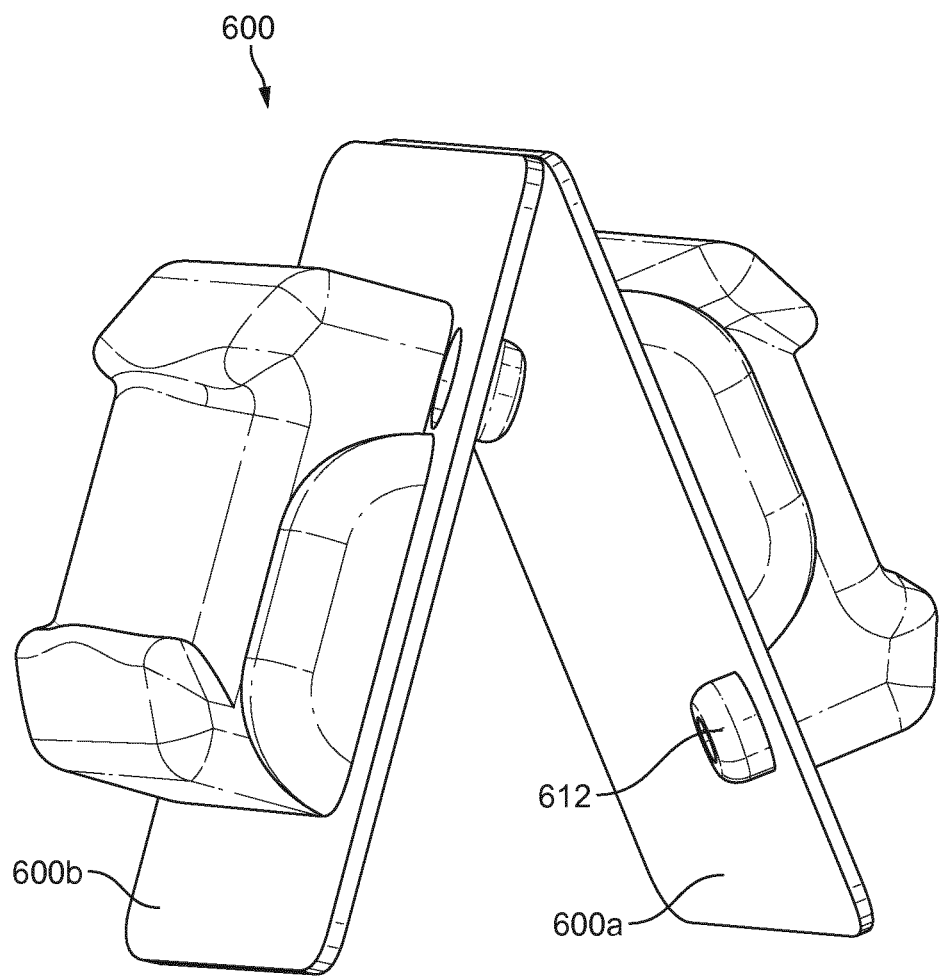
Figure 18C:
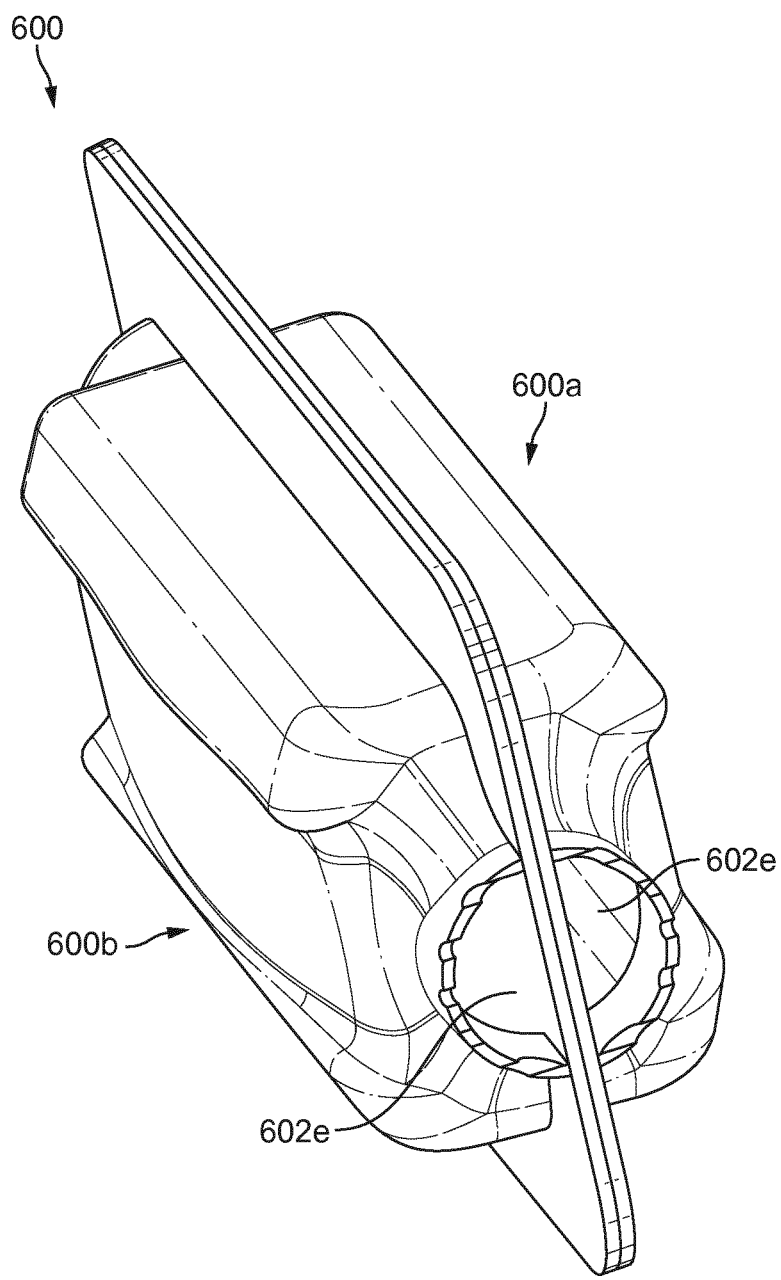

As is best seen in FIG. 18a to FIG. 18c, in this third example, similarly to the second example described above, the cartridge 600 is a dual-body arrangement comprising a first cartridge body 600a and a second cartridge body 600b. Each of the first cartridge body 600a and the second cartridge body 600b comprises a respective protective cover 602, 602' attached to, for example adhered to, to a respective planar base 604, 604'. Each cover 602, 602' and the planar base 604, 604' to which it is attached together define a chamber for containing the aerosol generating material (not shown). The planar base 604 is substantially parallel to the longitudinal axis of the first cartridge body 600a and the planar base 604' is substantially parallel to the longitudinal axis of the second cartridge body 600b.

Each planar base 604, 604' is substantially rectangular in shape. Each protective cover 602, 602' comprises a main elongate central section 602a, 602a and smaller first 602b and second 602c end sections at respective ends of the main elongate central section 602a, 602a'. As with the cartridge 200 of the first example and the cartridge 400 of the second example, the planar bases 604, 604' are formed of a sheet of thermally conductive material, for example, metal foil such as aluminum foil, and the protective covers 602, 602' may be formed any of the materials described above with respect to the first and second examples and adhered to the planar bases 604, 604' using a suitable adhesive as also described above with respect to the first and second examples.

In this third example, and differently to the second example described above, in a pre-use configuration, rather than being joined in an "end-to-end" relationship, the planar bases 604, 604' are joined in a "side-to-side" relationship by being connected together at sides parallel to the longitudinal axis of the cartridge 600 along a line of weakening 608.

In order to insert a cartridge 600 into the apparatus 500, a user takes a cartridge 600 in the "prior to use" configuration shown in FIG. 18a and folds the planar bases 604, 604' towards one another about the weakening line 608 until the planar bases 604, 604' are orientated in a position similar to that shown in FIG. 18b.

The user may then arrange the cartridge 600 in the interior of the heater support section 607 with the heater 513 between the planar bases 604, 604' and continue to fold the planar bases 604, 604' together until the heater 513 is sandwiched between them. In this position, at least a major portion or all of the bottom surface of the planar base 604 is against the first surface 513a of the heater 513 and at least a major portion or all of the bottom surface of the planar base 604' is against the second surface of the heater 513.

Each of the first cartridge body 600a and the second cartridge body 600b comprises a respective member 612, 612', which in this example is in the form of a short tube that is open at both of its end and extends through a planar base 604, 604' defining a passage through that planar base 604, 604' from one side to the other. Each member 612, 612' is located outside of a cover 602, 602' but directly adjacent to a central section 602a, 602a' and a second end section 602, 602'. Each member 612, 612' protrudes away from the underside of the planar base 604, 604' that it extends through.

As is best appreciated from FIGS. 18b and 18c (which for clarity do not illustrate the heater 513), when the planar bases 604, 604' are folded so that the heater 613 is sandwiched between them, the member 612' punctures through the planar base 604 of the first cartridge body 600a in a region beneath the second 602c end section of the cover 602 of the first cartridge body 600a. Likewise, the member 612 punctures through the planar base 604' of the second cartridge body 600b in a region beneath the second 602c' end section of the cover 602' of the second cartridge body 600b'. Accordingly, the ends of the members 612, 612' that puncture through the planar bases 604, 604' are preferably sharpened or pointed or the like in order to facilitate this puncturing. As will be explained in more detail below, the member 612 acts as an inlet for the second cartridge body 600b and the member 612' acts as an inlet for the first cartridge body 600a. The first cover end sections 602b, 602b' have respective open ends 602e, 602e' that act as respective outlets for the first cartridge body 600a and the second cartridge body 600b. These open ends 602e, 602e' may be provided with a protective layer (not shown), to keep the material inside fresh, and which is peeled away by a user prior to inserting the cartridge 600 in the apparatus 500.

In addition, or alternatively, the first cover end sections 602b, 602b' may be provided with lines of weakening (as described above with respect to the cartridge 400) and be connected to corresponding first cover end sections (not shown) of corresponding first and second cartridge bodies (not shown) of a corresponding dual body cartridge (not shown) in a pack of such dual body cartridges. The dual body cartridge 600 may be broken free, by a user, from such pack, prior to be being inserted into the apparatus 500. It will be appreciated that in such a pack, any side of any given planar base may be connected to any side of any other given planar base by a line of weakening to enable a cartridge to be separated by a user from the pack.

Figure 19A:
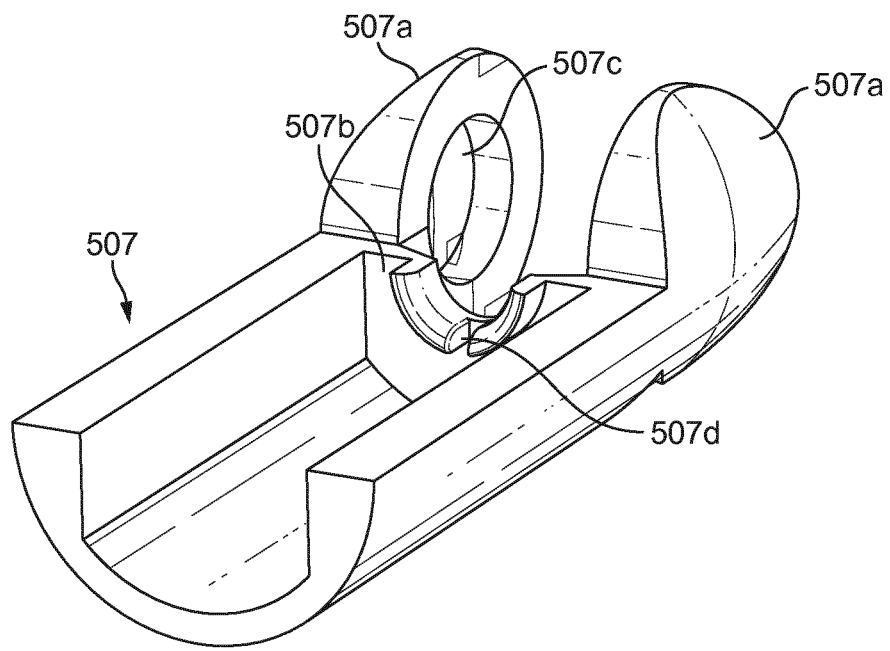
FIG. 19a shows a schematic perspective view of a heater support section of the third example of an apparatus for heating an aerosol generating material.

As is best appreciated from FIG. 19a, the heater support section 507 is generally "U" shaped in cross section and comprises a pair of opposing lobes 507a extending from opposite sides of one end 507b of the heater support section 507 parallel to its longitudinal axis. Each of the pair of lobes 507a defines a respective one of a pair of opposing recesses 507c (only one is visible in FIG. 19a). In this example, the recesses 507c have a generally circular cross section. The one end 507b also defines a first half 507d of a gasket for receiving the open ends 602e, 602e' of the cartridge 600.

Figure 19B:
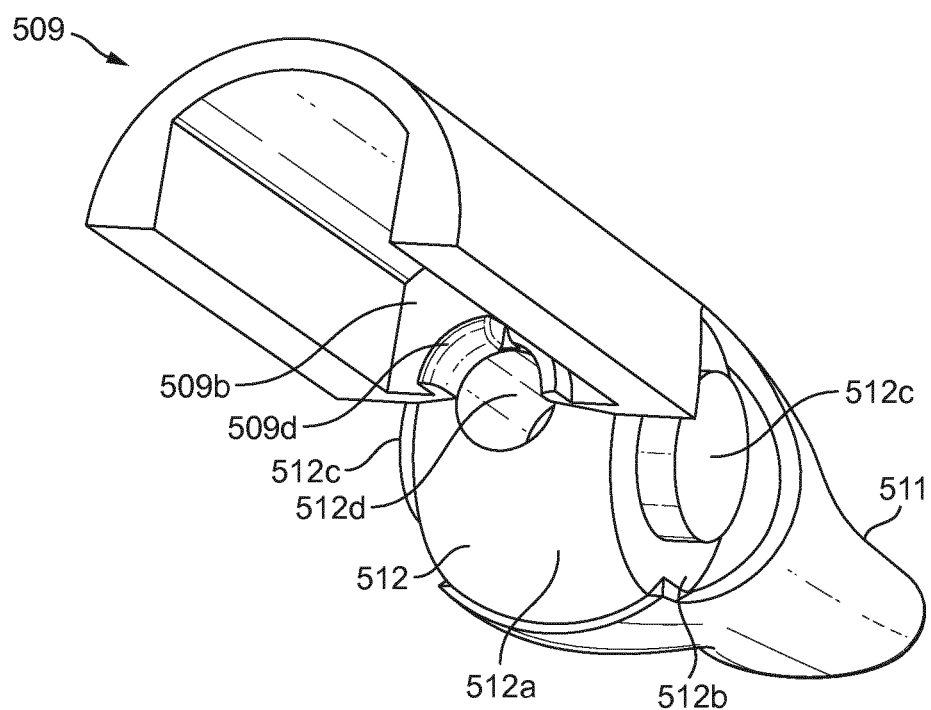
FIG. 19b shows a schematic perspective view of a lid section and a mouthpiece section of the third example of an apparatus for heating an aerosol generating material.

As is best appreciated from FIG. 19b, the lid section 509 is also substantially "U" shaped in cross section. The lid section 509 and the mouthpiece 511 are both mounted on a joint 512 that enables the lid section 509 and mouthpiece 511 to be pivoted with respect to the heater support section 507 between the open and closed positions.

In this example, the joint 512 comprises a part spherical body 512a that has a pair of circular end faces 512b (only one of which is visible in FIG. 19b). Each end face 512b has a respective lug 512c, which in this example is cylindrical in shape, extending therefrom. Each lug 512c is received in a respective one of the recesses 507c so that the joint 512 is supported between the opposing lobes 507a of the heater support section 507 and can rotate about an axis that is transverse to the longitudinal axis of the apparatus 500 to enable the lid section 509 and mouthpiece 511 to be pivoted between the open and closed positions.

One end 509b of the lid section defines a second half 509d of the gasket for receiving the open ends 602e, 602e' the cartridge 600. Each of the halves 507d, 509d of the gasket is semi-circular in cross-section such that the gasket is circular in cross section when the two halves 507d, 509d are brought together (i.e. when that apparatus 600 is in the closed configuration). In the closed configuration, the gasket is aligned with an aperture 512d that is formed all of the way through the joint 512. Accordingly, the gasket is in fluid communication with the outlet 611a of the mouthpiece 611.

As with the second example described above, in use, when a user actuates the actuator (not shown), the control circuitry 521 is operated so that electrical current flows through the resistive heating elements (not shown) formed on the first and second heating surfaces 513a to cause the heater 513 to heat up so that the first heater surface 513a heats the aerosol generating material in the first cartridge body 600a and the second heater surface heats the aerosol generating material in the second cartridge body 600b. Again, as the planar bases 604, 604' are formed of a thermally conductive material and are in good thermal contact with the heater 513, heat is very efficiently transferred to the aerosol generating material in each cartridge body 600a, 600b. This causes at least one component of the aerosol generating material in each cartridge body 600a, 600b to volatilize without combusting the aerosol generating material.

When the user draws on the mouthpiece 611, this causes a reduction in pressure in each cartridge body 600a, 600b, which causes air to be drawn into each cartridge body 600a, 600b via the air inlet 508 of the section 507b and the respective air inlets defined by the members 612' and 612. Typically, this air flow causes the volatilized component(s) of the aerosol generating material to be cooled, so that it/they condense to form an aerosol either inside each cartridge body 600a, 600b, inside the mouthpiece 511 or inside both. The user's continued drawing causes the airflow and aerosol to be drawn into the user's mouth via the mouthpiece 511. This can be repeated until the volatile component(s) is/are exhausted.

When all, or substantially all, of the volatile component(s) of the aerosol generating material in the cartridge 600 has/have been spent, the user opens the lid section 509, removes the cartridge 600 and inserts another unspent cartridge 600 into the channel and repeats the above process.

As described above with respect to FIGS. 7 to 14, in some examples the resistive heating elements (not shown) formed on the first and second heating surfaces 513a may be controlled independently of each other so that the aerosol generating material in each cartridge body 600a, 600b can be heated independently of each other in different time intervals. Again, the aerosol generating material may be different in each cartridge body 600a, 600b, for example, one cartridge may contain a flavored material. Again, the heater 513 may comprises a heat insulating layer (not shown) to inhibit heat being transferred from one side of the heating 513 to the other.

In some examples, the heat conducting material of any of the above examples is a non-porous material, such as aluminum. Providing a non-porous material as the heat-conducting material means that the heater and the housing holding the heater stays clean, as upon heating, the aerosol produced does not pass to the heater and create a build-up of material.

In some examples, the planar base and/or the protective cover of any of the examples above is provided with one or more score lines and/or embossments, for example, at the position in which the protrusions are configured to pierce the planar base and/or protective cover. The score lines and/or embossments act to reduce the strength of the planar base and/or the protective cover the piercing location such that less force is required to pierce them.

In some examples, any of the protrusions discussed in the examples above may include a gasket to provide a seal to the pierced area.

In at least some of examples described above, the aerosol generating material may be in the form of an aerosol generating material, for example a gel, that is a layer on, for example adhered to, the inner surface of the or each planar base of a cartridge. Furthermore, at least a portion of the inner surface of each planar base on which the aerosol generating material is received may be roughened. Surprisingly, it has been observed that having a rough surface on which the aerosol generating material is on may help prevent the aerosol generating material separating (e.g. de-laminating) from that surface during heating which would reduce the effectiveness of the heating process.

Figure 20A:
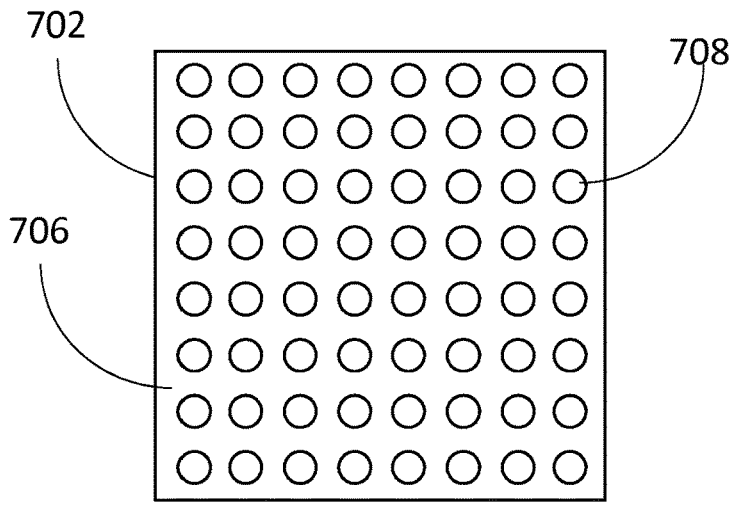
FIGS. 20A and 20B shows a schematic plan and perspective view of the first example of a first inner layer with a rough first surface for receiving an aerosol generating gel.
Figure 20B:
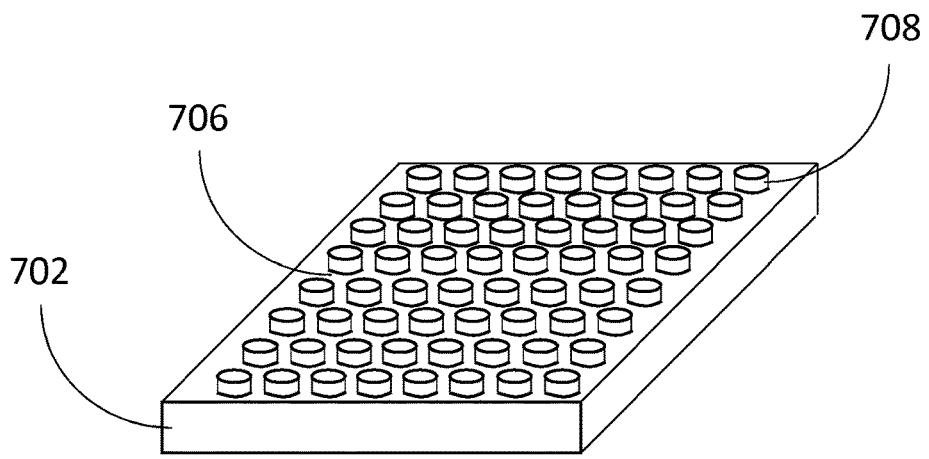

FIGS. 20A and 20B show an example of a first inner surface 706 of the first sheet of heat conducting material 702 of a first base, in which the first inner surface is rough to provide an uneven or irregular surface.

The aerosol forming material (not shown) will be located on the first inner surface 706 of the first sheet of heat conducting material 702. In the example shown in FIGS. 20A and 20B, the first inner surface 706 is rough due to the fact that there are a plurality of protuberances 708. In one example, the first surface 206 is made rough by making a number of holes in the support layer 202. The holes may be made by penetrating the first surface 206 with a pin.

In the example shown in FIGS. 20A and 20B, the protuberances take the form of cylinders, however, any shape that projects from the first inner surface of the heat conducting material may be used, such as cubes, pyramids and irregular shapes. It is not necessary for the protuberances 708 to be formed of the same shape. The protuberance 708 in FIGS. 20A and 20B are shown as covering most of the first surface 706 of the heat conducting material 702, but in other examples, the protuberances 708 only cover part of the first surface 706 of the heat conducting material 702.

In one example the protuberances 708 have a height of between 0.1 mm and 0.2 mm and a width of between 0.2 mm and 0.4 mm, and more preferably have a height of 0.15 mm and a width of 0.3 mm.

In one example, the first surface 706 of the heat conducting material is embossed to create the surface roughness. The protuberances 708 may also be formed by embossing.

Embossing the first inner surface 706 of the heat conducting material is a simple and repeatable way of creating a rough surface. The embossment may take the form of one or more logos. The first inner surface 706 may be made rough by including one or more ridges, folds, indents and raised sections.

The first inner surface 706 may be embossed using various patterns, such as one or more of spirals, lines; and/or squares.

Figure 20C:
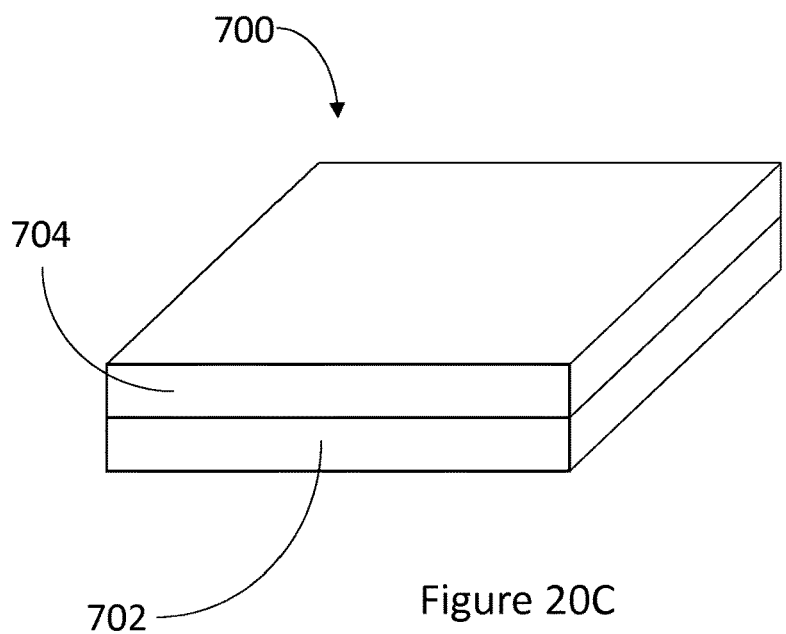
FIG. 20C shows a schematic perspective view of a first example of article for use with an apparatus for heating aerosol generating gel to volatilize at least one component of the aerosol generating gel.

The rough first inner surface 706 of the heat conducting material 702, as shown in FIGS. 20A and 20B, acts to increase the contact surface area between the aerosol generating material 704 and the heat conducting material 702. An example of article 700 formed from the heat conducting material 702 with a rough first inner surface 706 and aerosol generating material 704 is shown in FIG. 20C. The increased surface area will increase the adhesion between the aerosol forming material 704 and the heat conducting material 702, and hence reduce the likelihood of the aerosol generating material 704 separating from the first inner surface 706 of the heat conducting material 702.

Figure 21:
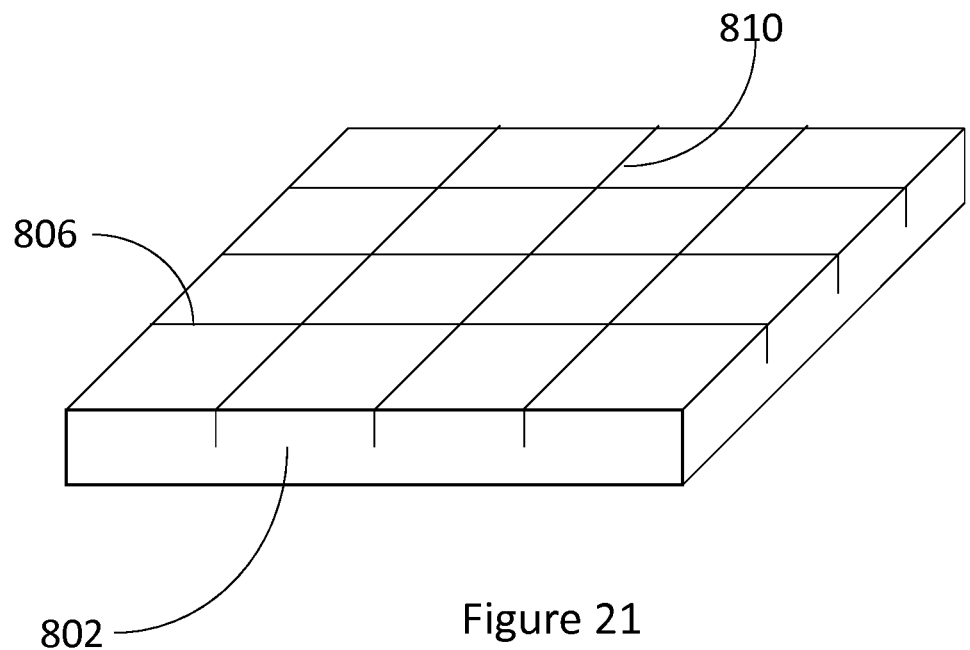
FIG. 21 shows a schematic perspective view of a support layer of the article with score lines.

In the further example shown in FIG. 21, the first inner surface 806 of the heat conducting material 802 is made rough by having one or more score lines 810 formed in the first inner surface 806. FIG. 21 shows the heat conducting material 802 with six score lines 810 applied to the first inner surface 806, however, in some examples there are fewer than six score lines and in other examples there are more than six score lines 810 applied to the first inner surface 806. As with the perturbations 708 shown in FIG. 20B, score lines 810 perform the function of adding a surface roughness to the first surface of the heat conducting material 806, which increases the adhesion between the aerosol generating material 804 and the layer 802. In one example, the surface roughness of the first inner surface 806 of the heat conducting material is provided by the score lines 810. In other examples, the surface roughness of the first inner surface 806 of the heat conducting material is provided by a combination of the perturbations 708 and the score lines 810.

Figure 22:
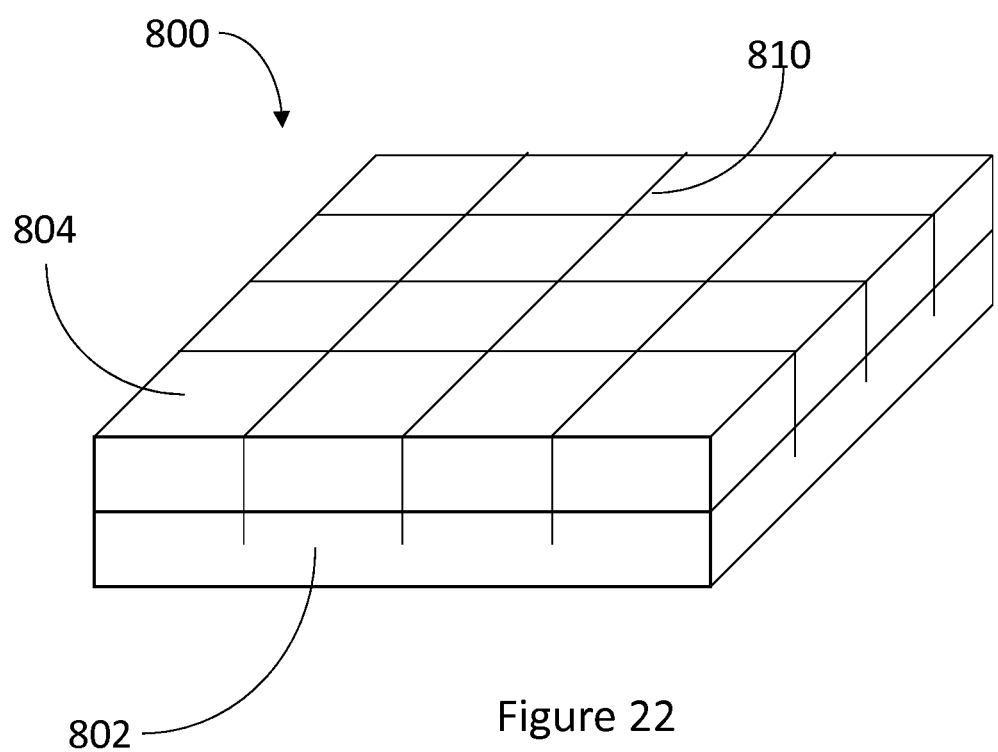
FIG. 22 shows a schematic perspective view of a second example of an article for use with an apparatus for heating aerosol generating agent to volatilize at least one component of the aerosol generating agent.

As shown in FIG. 22, the score lines 810 may also be applied to the aerosol generating material 804. Applying score lines 810 to the aerosol generating material 804 results in the aerosol generating material 804 being pooled into one or more separate sections delineated by the score lines 810. Separating the aerosol generating material 804 into separate sections provides more flow paths for any volatilized components and the outer surface of the aerosol generating material 804.

In the example of the aerosol generating material comprising an aerosol generating gel, the gel 704 and 804 may be formed from different tobacco extracts, such as Burley, Virginia and Oriental. Aerosol generating gels 704, 804 formed from different tobacco extracts may have different properties, for example, gels formed from Burley tobacco is more brittle, whereas gels formed from Virginia and Oriental is more pliable.

Embodiments of the invention are configured to comply with applicable laws and/or regulations, such as, by way of non-limiting example, regulations relating to flavors, additives, emissions, constituents, and/or the like. For example, the invention may be configured such that a device implementing the invention is compliant with applicable regulations before and after adjustment by a user. Such implementations may be configured to be compliant with applicable regulations in all user-selectable positions. In some embodiments, the configuration is such that a device implementing the invention meets or exceeds required regulatory test(s) in all user-selectable positions, such as, by way of non-limiting example, the testing threshold(s)/ceiling(s) for emissions and/or smoke constituents.

The various embodiments described herein are presented only to assist in understanding and teaching the claimed features. These embodiments are provided as a representative sample of embodiments only, and are not exhaustive and/or exclusive. It is to be understood that advantages, embodiments, examples, functions, features, structures, and/or other aspects described herein are not to be considered limitations on the scope of the invention as defined by the claims or limitations on equivalents to the claims, and that other embodiments may be utilized and modifications may be made without departing from the scope of the claimed invention. Various embodiments of the invention may suitably comprise, consist of, or consist essentially of, appropriate combinations of the disclosed elements, components, features, parts, steps, means, etc, other than those specifically described herein. In addition, this disclosure may include other inventions not presently claimed, but which may be claimed in future.

The invention claimed is:

1. A cartridge for use with an apparatus for heating aerosol generating material to volatilize at least one component of the aerosol generating material, the cartridge comprising:
    a first body defining a first chamber, wherein the first body comprises a first base comprising a sheet of heat conductive material and having a first outer surface; and
    aerosol generating material located within the first chamber;
    wherein at least a major portion of the first outer surface of the first base is adapted to contact a first heating surface of a heater of the apparatus for heating the aerosol generating material within the first chamber, and wherein the first base is substantially parallel to a longitudinal axis of the first body;
    wherein the cartridge further comprises:
        a second body defining a second chamber, wherein the second body comprises a second base comprising a sheet of heat conductive material having a second outer surface; and
        aerosol generating material located within the second chamber;
        wherein at least a major portion of the second outer surface of the second base is adapted to contact a second heating surface of the heater of the apparatus, and wherein the second base is substantially parallel to a longitudinal axis of the second body; and
    wherein the first base and the second base are connected together to enable relative pivotal movement of the first base and the second base so that a user can bring the first outer surface into contact with the first heating surface of the heater and the second outer surface into contact with the second heating surface of the heater.

2. The cartridge according to claim 1, wherein the sheet of heat conductive material is flexible.

3. The cartridge according to claim 1, wherein the first body comprises a first cover attached to the first base, wherein the first cover and the first base define the first chamber.

4. The cartridge according to claim 3, wherein the first cover comprises a first portion and a second portion at one end of the first portion, wherein the first portion is wider than the second portion.

5. The cartridge according to claim 4, wherein the first cover comprises a third portion at another end of the first portion, wherein the first portion is wider than the third portion.

6. The cartridge according to claim 1, wherein the first base and the second base are connected along a first line of weakening to enable the relative pivotal movement.

7. The cartridge according to claim 6, wherein the first line of weakening is one of a perforated line, a serrated line or a cut line.

8. The cartridge according to claim 1, wherein the first base and the second base are, in a pre-use configuration, connected at respective sides of the first base and the second base that are substantially perpendicular to a longitudinal axis of the cartridge.

9. The cartridge according to claim 8, wherein the second body comprises a second cover attached to the second base, wherein the second cover and the second base define the second chamber, and wherein the first cover and the second cover are, in the pre-use configuration, connected along a second line of weakening which ruptures when the first base and the second base undergo relative pivotable movement, whereby the first cover and the second cover are separated to provide at least one of a volatilized material and an aerosol outlet for the first cover and at least one of a volatilized material and an aerosol outlet for the second cover.

10. The cartridge according to claim 9, wherein the first base comprises a first piercer and the second base comprises a second piercer.

11. The cartridge according to claim 10, wherein the first piercer is for piercing the second base to provide an air inlet for the second chamber and the second piercer is for piercing the first base to provide an air inlet for the first chamber.

12. The cartridge according to claim 11, wherein the first cover comprises a first portion and a second portion at one end of the first portion, wherein the first portion is wider than the second portion, wherein the second piercer is positioned on the second base so as to pierce the first base at a point covered by the second portion of the first cover.

13. The cartridge according to claim 11, wherein the second cover comprises a first portion and a second portion at one end of the first portion, wherein the first portion is wider than the second portion, wherein the first piercer is positioned on the first base so as to pierce the second base at a point covered by the second portion of the second cover.

14. The cartridge according to claim 1, wherein the first base and the second base are, in a pre-use configuration, connected at respective sides of the first base and the second base that that are substantially parallel to a longitudinal axis of the cartridge.

15. The cartridge according to claim 14, wherein the second body comprises a second cover attached to the second base, wherein the second cover and the second base define the second chamber.

16. The cartridge according to claim 15, wherein the first base comprises a first piercer and the second base comprises a second piercer.

17. The cartridge according to claim 16, wherein the first piercer is for piercing the second base to provide an air inlet for the second chamber and the second piercer is for piercing the first base to provide an air inlet for the first chamber.

18. The cartridge according to claim 16, wherein the first cover comprises a first portion and a second portion at one end of the first portion, wherein the first portion is wider than the second portion, wherein the second piercer is positioned on the second base so as to pierce the first base at a point covered by the second portion of the first cover.

19. The cartridge according to claim 17, wherein the second cover comprises a first portion and a second portion at one end of the first portion, wherein the first portion is wider than the second portion, wherein the first piercer is positioned on the first base so as to pierce the second base at a point covered by the second portion of the second cover.

20. The cartridge according to claim 9, further comprising a heat resistant adhesive adhering the second cover to the second base, wherein the heat resistant adhesive is only provided in regions where the second cover is adhered to the second base.

21. The cartridge according to claim 1, wherein the sheet of heat conductive material includes a first inner surface and at least a portion of the first inner surface is rough, wherein the aerosol generating material is located on the portion of the first inner surface that is rough.

22. The cartridge according to claim 21, wherein the portion of the first inner surface that is rough comprises a plurality of protuberances.

23. The cartridge according to claim 21, wherein the portion of the first inner surface is embossed.

24. The cartridge according to claim 21, wherein the portion of the first inner surface includes one or more score lines or holes.

25. The cartridge according to claim 24, wherein the aerosol generating material is separated into one or more sections based on the one or more score lines.

* * * * *